United States Patent [19]

Biftu et al.

[11] Patent Number: 4,977,146

[45] Date of Patent: Dec. 11, 1990

[54] 2,5-DIARYL TETRAHYDROFURANS AND ANALOGS THEREOF AS PAF ANTAGONISTS

[75] Inventors: Tesfaye Biftu, Parlin; Mitree M. Ponpipom, Branchburg; Nirindar N. Girotra, Old Bridge, all of N.J.

[73] Assignee: Merck & Co., Inc., Rahway, N.J.

[21] Appl. No.: 505,712

[22] Filed: Apr. 11, 1990

Related U.S. Application Data

[63] Continuation-in-part of Ser. No. 362,920, Jun. 8, 1989, abandoned.

[51] Int. Cl.$^5$ .................. C07D 307/12; C07D 307/14
[52] U.S. Cl. ...................... 514/99; 514/461; 514/471; 549/218; 549/491; 549/496; 549/500; 549/501; 549/502
[58] Field of Search ............... 549/218, 491, 496, 500, 549/501, 502; 514/99, 461, 471

[56] References Cited

U.S. PATENT DOCUMENTS 3,769,350 10/1973 Perry et al. .................. 549/362 X
4,539,332 9/1985 Biftu et al. .................. 514/461
4,595,693 5/1986 Biftu et al. .................. 514/461
4,757,084 7/1988 Biftu et al. .................. 514/438

FOREIGN PATENT DOCUMENTS 0144804 6/1985 European Pat. Off. .
0154857 9/1985 European Pat. Off. .
0199324 10/1986 European Pat. Off. .
0217204 4/1987 European Pat. Off. .

OTHER PUBLICATIONS

Chem. Abstracts, vol. 96, Abstract 122588a (1982).
Biftu, T., Hazra, G. B. Stevenson, R., and Williams, J. R., Synthesis of Lignans, 2,3-diaroylbutanes J. Chem. Soc. pp. 1147-1150 (1978).
Biftu, T., Hazra, G. B., Stevenson, R., Synthesis of (+)-Deoxyschizandrin, J. Chem. Soc. pp. 2276-2281 (1979).
Chem. Abstracts, vol. 83, Abstract 8676g (1975).
Chem. Abstracts, vol. 86, Abstract 1648v (1977).
Chem. Abstracts, vol. 90, Abstract 54764z (1979).
Chem. Abstracts, vol. 42. Abstract 5836e (1948).
Chem. Abstracts, vol. 79, Abstract 136925u (1973).
Chem. Abstracts, vol. 81, Abstract 135662k (1974).
Hwang, S. B., Lam, M. H., Biftu, T., Beattie, T. R., Asghen, T. Y., Trans-2,5-bis(3,4,5-trimethoxyphenyl) tetrahydrofuran, J. Biol. Chem, vol. 260, No. 29, pp. 15639-15645 (Dec. 1985).
Sarkanen, K. V. and Wallis, A. F. A., Oxidative Dimerization's of (E)-and (2)-Isoeugenol (2-Methoxy-4-propenylphenol) and (E)-(Z)-2,6-dimethoxy-4-propenyl-phenol, J. Chem. Soc., Perkin Transactions, pp. 1869-1878 (1973).
Stevenson, R., Williams, J. R., Synthesis of Tetrahydrofuran Lignans, (+)-Galbelgin and (+)-Grandisin, Tetrahedron, vol. 33, pp. 285-288 (1977).

Primary Examiner—Richard L. Raymond
Attorney, Agent, or Firm—Curtis C. Panzer; Hesna J. Pfeiffer

[57] ABSTRACT

The present invention is directed to a specifically substituted tetrahydrofuran of the formula (I)

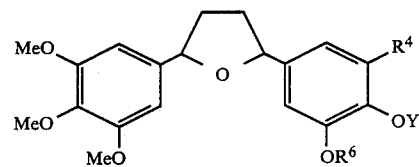

wherein $R^4$ is an alkylthio, alkylsulfinyl or alkylsulfonyl containing group, Y is an alkyl or substituted alkyl group, $R^6$ is an alkyl or a substituted alkyl group and the substituents at positions 3, 4 or 5 are acyclic.

30 Claims, No Drawings

2,5-DIARYL TETRAHYDROFURANS AND ANALOGS THEREOF AS PAF ANTAGONISTS

RELATED U.S. APPLICATION DATA

The instant application is a continuation-in-part of U.S. Ser. No. 362,920 filed June 8, 1989, now abandoned.

BACKGROUND OF THE INVENTION

Platelet activating factor (PAF) has recently been identified as an acetyl glyceryl ether phosphorylcholine (AGEPC), i.e., 1-0-hexadecyl/octadecyl-2-acetyl-sn-glyceryl-3-phosphorylcholine (Hanbahan D. J., et al., *J. Biol. Chem.* 255:5514, 1980). Even before its chemical identification, PAF had been linked to various biological activities and pathways making it one of the important mediators responsible for a variety of physiological processes including activation or coagulation of platelets, pathogenesis of immune complex deposition, smooth muscle contraction, inflammation, hypotension, shock, pain, edema as well as respiratory, cardiovascular and intravascular alterations. Since these physiological processes are in turn associated with a large group of diseases, for example, inflammatory disease, cardiovascular disorder, hypotension, shock, psoriasis, allergic and skin diseases, asthma, lung edema, peptic or stomach ulcer, dental pain, and adult respiratory distress syndrome, more and more scientific investigation has been focused on the search of a PAF antagonist or inhibitor for treating or preventing these common diseases.

The compounds of the present invention are specific PAF antagonists. They are similar to a subclass of compounds called lignans which characteristically contain two phenylpropyl groups bonded at the β-carbon. Tetrahydrofuran (THF) derivatives can exist in eight different stereochemical configurations as shown in Scheme I.

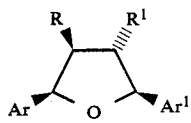
(1)

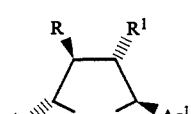
(2)

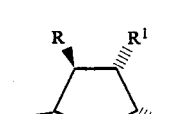
(3)

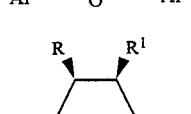
(4)

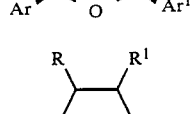
(5)

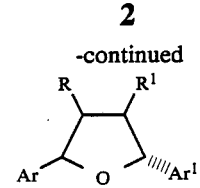
(6)

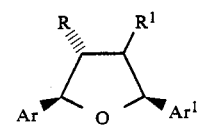
(7)

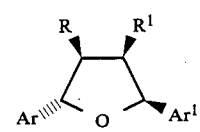
(8)

We have been able to prepare all the possible isomers of the tetrahydrofuran lignan analogs with different substituents and found that activity is stereospecific.

Accordingly, the present invention is directed to the preparation of the most potent isomers of known or novel tetrahydrofuran derivatives as PAF antagonists and use them for the treatment of various diseases including prevention of platelet aggregation, hypotension, inflammation, asthma, lung edema adult respiratory distress syndrome, various shock syndromes including septic shock, cardiovascular disorders and other related skeletal muscular disorders, graft-host rejection, nephritis including glomerulo nephritus, pancreatitis, lupus, idiopathic thrombocytopenic purpura, inflammatory bowel disease, psoriasis and dermatitis.

The present invention is also directed to acceptable pharmaceutical compositions containing one or more of the tetrahydrofuran derivatives and/or analogs as the active ingredient. As PAF antagonists, these novel compositions should be effective in the treatment of various skeletal muscular related diseases.

The present invention is also directed to a method of treatment comprising the administration of a therapeutically sufficient amount of these PAF antagonists to a patient suffering from various skeletal muscular disorders including inflammation, e.g., osteoarthritis, rheumatoid arthritis and gout, hypotension, shock including septic shock, psoriasis, allergic or skin diseases, asthma, pain especially dental pain, peptic or stomach ulcer, lung edema, adult respiratory distress syndrome or cardiovascular disorders graft-host rejection, nephritis including glomerulo nephritus, pancreatitis, lupus, idiopathic thrombocytopenic purpura, inflammatory bowel disease and dermatitis.

BRIEF DESCRIPTION OF THE INVENTION

The present invention is directed to a specifically substituted tetrahydrofuran of formula (I)

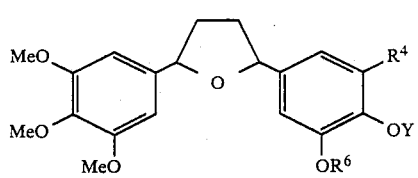

wherein $R^4$ is an alkylthio, alkylsulfinyl or alkylsulfonyl containing group, Y is an alkyl or substituted alkyl group, $R^6$ is an alkyl or a substituted alkoxy and the substituents at positions 3,4 or 5 are acyclic.

DETAILED DESCRIPTION OF THE INVENTION

The present invention is directed to compounds of the following structural formula (I):

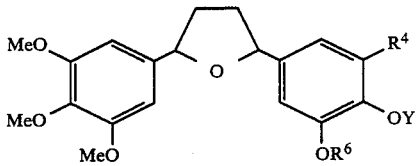

or a pharmaceutically acceptable salt thereof wherein:
$R^4$ is $S(O)_nR^2$ in which n is 0,1 or 2 and $R^2$ is selected from the group consisting of
  (a) $C_{2-6}$alkyl,
  (b) Substituted $C_{1-6}$alkyl wherein the substituent is selected from the group consisting of hydroxy, amino, N—$C_{1-4}$alkylamino, and N,N—$C_{1-4}$dialkylamino, and
  (c) $C_{1-6}$alkylcarbonyl-$C_{1-6}$alkyl;
Y is selected from the group consisting of
  (a) $C_{1-12}$alkyl,
  (b) $C_{1-6}$hydroxyalkyl,
  (c) $C_{1-6}$alkylcarbonyl-$C_{1-6}$alkyl, and
  (d) amino-$C_{1-6}$alkyl;
  (e) N-substituted or N,N-disubstituted amino-$C_{1-6}$alkyl wherein the substituents are each individually $C_{1-6}$alkyl;
$R^6$ is selected from the group consisting of
  (a) substituted $C_{1-6}$alkyl wherein the substituent is selected from the group consisting of hydroxy, amino, N—$C_{1-4}$alkylamino, N,N di-$C_{1-4}$alkylamino, and —O—$R^{10}$, wherein $R^{10}$ is
    (1) —$PO_2(OH)^- M^+$ wherein $M^+$ is a Pharmaceutically acceptable monovalent cation,
    (2) —$SO_3^- M^+$, or
    (3) —$C(O)(CH_2)_2$—$CO_2^- M^+$,
  (b) $C_{1-6}$alkylcarbonyl-$C_{1-6}$alkyl, or
  (c) $C_{1-6}$carboxyalkyl.

As will be understood by those skilled in the art, pharmaceutically acceptable salts include, but are not limited to salts with inorganic acids such as hydrochloride, sulfate, phosphate, diphosphate, hydrobromide, and nitrate or salts with an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to hydrogen, sodium, potassium, calcium, aluminum, magnesium, barium, zinc, lithium, ammonium, or an amino acid including glycine, alanine, valine, leucine, isoleucine, serine, threonine, aspartic acid, asparagine, glutamic acid, glutamine, lysine, hydroxylysine, histidine, arginine, phenylalanine, tyrosine, tryptophan, thyroxine, cystine, cysteine, methionine, proline, hydroxyproline, ornithine, β-alanine, γ-amino butyric acid, sarcosine, betaine, homoserine, or citrulline; or mono, di or tri-$C_{1-6}$-alkylamino. For example, compounds wherein $R^{10}$ is —$PO_2(OH)^- M^+$ is intended to include the monopotassium, monolithium, and monosodium salts such as those of Example 26, infra.

Illustrating the invention is the class of compounds of the formula (I) wherein the substituents at positions 2 and 5 of the tetrahydrofuran are in a trans relationship to one another, and
Y is
  (a) $C_{1-6}$alkyl, or
  (b) $C_{1-4}$alkylcarbonyl-$C_{1-4}$alkyl.

A subclass of these compounds is the compounds of formula (I) wherein n is 2, and
$R^2$ is selected from the group consisting of
  (a) Substituted $C_{1-6}$alkyl wherein the substituent is selected from the group consisting of hydroxy amino, N—$C_{1-4}$alkylamino, and N,N di-$C_{1-4}$alkylamino, and
  (b) $C_{1-4}$alkylcarbonyl-$C_{1-4}$alkyl.

A smaller subclass of these compounds is the compounds of formula (I) wherein $R^6$ is
  (a) substituted $C_{1-6}$alkyl wherein the substituent is selected from the group consisting of hydroxy, amino, N—$C_{1-4}$alkylamino, N,N-di-$C_{1-4}$alkylamino and —O—$R^{10}$, wherein $R^{10}$ is
    (1) —$PO_2(OH)^- M^+$ wherein $M^+$ is a pharmaceutically acceptable monovalent cation,
    (2) —$SO_3^- M^+$, OR
    (3) —$C(O)(CH_2)_2$—$CO_2^- M^-$, and
  (b) $C_{1-6}$alkylcarbonyl-$C_{1-6}$alkyl.

A still smaller subclass of these compounds is the compounds of formula (I) wherein
Y is n propyl or 2-oxopropyl.

Exemplifying this subclass are those compounds of the formula (I) which are:
(a) trans-2-[3-(2-Oxopropylsulfonyl)-4-n-propoxy-5-(3-(N,N-dimethylamino)-n-propoxy)phenyl]-5-(3,4,5-trimethoxyphenyl)tetrahydrofuran,
(b) trans-2-[3-(2-Oxopropylsulfonyl)-4-n-propoxy-5-(3-hydroxy-n propoxy)phenyl]-5-(3,4,5-trimethoxyphenyl)tetrahydrofuran,
(c) trans-2-[3-(2-Oxopropylsulfonyl)-4-n-propoxy-5-(3-phosphopropoxy)-phenyl]-5-(3,4,5-trimethoxyphenyl)tetrahydrofuran,
(d) trans-2-[3-(2-Oxopropylsulfonyl)-4-n-propoxy-5-(2-oxopropoxy)phenyl]-5-(3,4,5-trimethoxyphenyl)tetrahydrofuran,
(e) trans-2-[3-(2-hydroxy-n-propylsulfonyl)-4-n propoxy-5-(3-hydroxy-n-propoxy)phenyl]-5-(3,4,5-trimethoxyphenyl)tetrahydrofuran,
(f) trans-2-[3-(2-hydroxy-n-propylsulfonyl)-4-n-propoxy-5-(2-oxopropoxy)-phenyl]-5-(3,4,5-trimethoxyphenyl)tetrahydrofuran,
(g) trans-2-[3-(2-Amino-n-propyl-sulfonyl)-4-n-propoxy-5-(3-hydroxy-n-propoxy)phenyl]-5-(3,4,5-trimethoxyphenyl)tetrahydrofuran,
(h) trans-2-[3-(2-N-Methylamino-n-propyl-sulfonyl)-4-n-propoxy-5-(3-hydroxy-n-propoxy)phenyl]-5-(3,4,5-trimethoxyphenyl)tetrahydrofuran,
(i) trans-2-[3-(2-N,N-dimethylamino-propylsulfonyl)-4-n-propoxy-5-(3-hydroxy-n-propoxy)phenyl]-5-(3,4,5-trimethoxy-phenyl)tetrahydrofuran,
(j) trans-2-[3-(2-N-Ethylamino-n-propylsulfonyl)-4-n-propoxy-5-(3-hydroxy-n-propoxy)phenyl]-5-(3,4,5-trimethoxyphenyl)tetrahydrofuran,
(k) trans-2-[3-(2-N-Methylaminoethyl-sulfonyl)-4,5-di-n-propoxyphenyl]-5-(3,4,5-trimethoxyphenyl)tetrahydrofuran,
(l) trans-2-[3-(2-N,N-Dimethylaminoethylsulfonyl)-4,5-di-n-propoxyphenyl]-5-(3,4,5-trimethoxyphenyl)tetrahydrofuran,
(m) trans-2-[3-(2-Aminoethylsulfonyl)-4,5-di-n-propoxyphenyl]-5-(3,4,5-trimethoxyphenyl)tetrahydrofuran, (n) trans-2-[3-(2-N-Ethylaminoethyl-sulfonyl)-4,5-di-n-propoxyphenyl]-5-(3,4,5-trimethoxyphenyl)tetrahydrofuran, (o) trans-2-[3-(2-N-Propylaminoethyl-sulfonyl)-4,5-di-n-propoxyphenyl]-5-(3,4,5-trimethoxyphenyl)tetrahydrofuran, (p) trans-2-[3-(2-N,N-Dimethylaminoethylsulfonyl)-4-n-propoxy-5-(3-hydroxy-n-propoxy)phenyl]-5-(3,4,5-trimethoxyphenyl)tetrahydrofuran, (q) trans-2-[3-(2-N,N-Dimethylaminoethylsulfonyl)-4-n-propoxy-5-(2-oxo-propoxyphenyl]-5-(3,4,5-trimethoxyphenyl)tetrahydrofuran, (r) trans-2-[3-(2-Hydroxyethylsulfonyl)-4-n-propoxy-5-(2-oxo-propoxy)phenyl]-5-(3,4,5-trimethoxyphenyl)-tetrahydrofuran, (s) trans-2-[3-(2-N,N-Dimethylaminoethylsulfonyl)-4-n-propoxy-5-(2-hydroxy-n-propoxy)phenyl]-5-(3,4,5-trimethoxyphenyl)tetrahydrofuran, or a stereochemical isomer thereof in the (2S,5S) configuration.

Particularly exemplifying the invention are (a) trans-2-[3-(2-Oxopropylsulfonyl)-4-n-propoxy-5-(3-hydroxy-n-propoxy)phenyl]-5-(3,4,5-trimethoxyphenyl)tetrahydrofuran, (b) trans-2-[3-(2-Oxopropylsulfonyl)-4-n-propoxy-5-(3-phosphopropoxy)phenyl]-5-(3,4,5-trimethoxyphenyl)tetrahydrofuran, and (c) trans-2-[3-(2-hydroxy-n-propylsulfonyl)-4-n-propoxy -5-(3-hydroxy-n-propoxy)phenyl]-5-(3,4,5-trimethoxyphenyl)tetrahydrofuran, and (2S,5S) stereoisomers which are (d) trans-(2S,5S)-2-[3-(2-Oxopropylsulfonyl)-4-n-propoxy-5-(3-hydroxy-n-propoxy)phenyl]-5-(3,4,5-trimethoxyphenyl)tetrahydrofuran, (e) trans-(2S,5S) 2-[3-(2-Oxopropylsulfonyl)-4-n-propoxy-5-(3-phosphonopropoxy)phenyl]-5-(3,4,5-trimethoxyphenyl)tetrahydrofuran, and (f) trans-(2S,5S)-2-[3-(2-hydroxy-n-propylsulfonyl)-4-n-propoxy-5-(3-hydroxy-n-propoxy)phenyl]-5-(3,4,5-trimethoxyphenyl)tetrahydrofuran.

Further exemplifying the invention are (S,S,S) and (S,S,R) stereoisomers which are (a) (−)-trans-(2S,5S)-2-[3-{(2S)-2-Hydroxypropylsulfonyl)}-4-n-propoxy-5-(3-hydroxypropoxy)phenyl]-5-(3,4,5-trimethoxyphenyl)tetrahydrofuran and (b) (−)-trans-(2S,5S)-2-[3-{(2R)-2-Hydroxypropylsulfonyl)}-4-n-propoxy-5-(3-hydroxypropoxy)phenyl]-5-(3,4,5-trimethoxyphenyl)tetrahydrofuran.

Another embodiment within the scope of the invention are the compounds of formula (I):

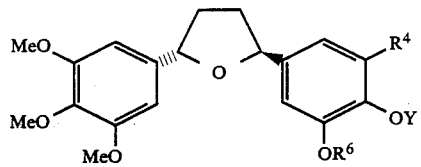

wherein:
$R^4$ is $SO_2CH_2COCH_3$ (2S,5S),
Y is —$CH_2CH_2CH_3$, and
$R^6$ is selected from —$(CH_2)_3$-O-$PO_2(OH)$— $M^+$, wherein M is as defined as above, and substituted —$(CH_2)_3$-O-$PO_2(OH)$—, wherein the substituent is

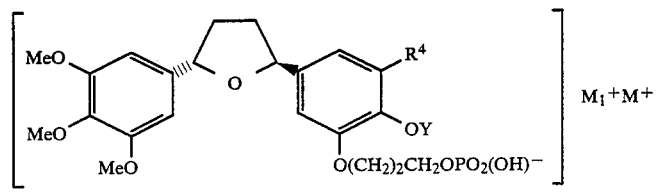

or

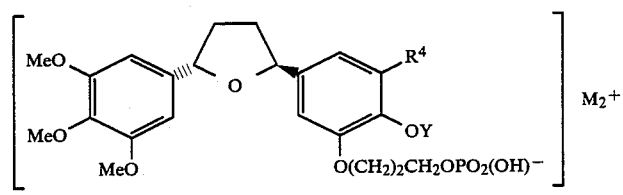

wherein $M_1$ is a pharmaceutically acceptable amino acid cation as described above and $M_2$ is a pharmaceutically acceptable di-valent cation as defined above.

A class of compounds within this embodiment is the compounds wherein $R^6$ is selected from —$(CH_2)_3$-O-$PO_2(OH)$— $M^+$, wherein M is sodium potassium ammonium or lithium, and substituted —$(CH_2)_3$-O-$PO_2$-$(OH)$—, wherein the substituent is

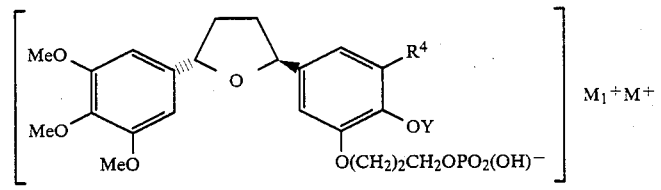

wherein

M is K and M₁ is ornithine,
M is Na and M₁ is ornithine,
M is Li and M₁ is ornithine,
M is K and M₁ is lysine,
M is Na and M₁ is lysine, or
M is Li and M₁ is lysine.

Exemplifying this class are (a) (−)-trans-(2S,5S)-[3-(2-Oxopropylsulfonyl)-4-n-propoxy-5-[3-(phosphonooxy)propoxy]phenyl]-5-(3,4,5-trimethoxyphenyl) tetrahydrofuran monopotassium salt, (b) (−)-trans-(2S,5S)-[3-(2-Oxopropylsulfonyl)-4-n-propoxy-5-[3-(phosphonooxy)propoxy]phenyl]-5-(3,4,5-trimethoxyphenyl) tetrahydrofuran monolithium salt, (c) (−)-trans-(2S,5S)-[3-(2-Oxopropylsulfonyl)-4-n-propoxy-5-[3-(phosphonooxy)propoxy]phenyl]-5-(3,4,5-trimethoxyphenyl) tetrahydrofuran monosodium salt, (d) (−)-trans-(2S,5S)-[3-(2-Oxopropylsulfonyl)-4-n-propoxy-5-[3-(phosphonooxy)propoxy]phenyl]-5-(3,4,5-trimethoxyphenyl) tetrahydrofuran potassium ornithine salt, (e) (−)-trans-(2S, 5S)-[3-(2-Oxopropylsulfonyl)-4-n-propoxy-5-[3-(phosphonooxy)propoxy]phenyl]-5-(3,4,5-trimethoxyphenyl) tetrahydrofuran sodium ornithine salt, (f) (−)-trans-(2S, 5S)-[3-(2-Oxopropylsulfonyl)-4-n-propoxy-5-[3-(phosphonooxy)propoxy]phenyl]-5-(3,4,5-trimethoxyphenyl) tetrahydrofuran sodium ornithine salt, (g) (−)-trans-(2S, 5S)-[3-(2-Oxopropylsulfonyl)-4-n-propoxy-5-[3-(phosphonooxy)propoxy]phenyl]-5-(3,4,5-trimethoxyphenyl) tetrahydrofuran potassium lysine salt, (h) (−)-trans-(2S, 5S)-[3-(2-Oxopropylsulfonyl)-4-n-propoxy-5-[3-(phosphonooxy)propoxy]phenyl]-5-(3,4,5-trimethoxyphenyl) tetrahydrofuran sodium lysine salt, and (i) (−)-trans-(2S, 5S)-[3-(2-Oxopropylsulfonyl)-4-n-propoxy-5-[3-(phosphonooxy)propoxy]phenyl]-5-(3,4,5-trimethoxyphenyl) tetrahydrofuran lithium lysine salt.

Particularly exemplifying this embodiment are (a) (−)-trans-(2S, 5S)-[3-(2-Oxopropylsulfonyl)-4-n-propoxy-5-[3-(phosphonooxy)propoxy]phenyl]-5-(3,4,5-trimethoxyphenyl) tetrahydrofuran monopotassium salt, (b) (−)-trans-(2S, 5S)-[3-(2-Oxopropylsulfonyl)-4-n-propoxy-5-[3-(phosphonooxy)propoxy]phenyl]-5-(3,4,5-trimethoxyphenyl) tetrahydrofuran potassium lysine salt, and (c) (−)-trans-(2S, 5S)-[3-(2-Oxopropylsulfonyl)-4-n-propoxy-5-[3-(phosphonooxy)propoxy]phenyl]-5-(3,4,5-trimethoxyphenyl) tetrahydrofuran sodium lysine salt.

Further, as is appreciated by those of ordinary skill in the art, applicants have used the terms "phospho" and "phosphono oxy" interchangeably in describing such compounds as the fourth and fifth compound in Table I.

The compounds of formula I may be prepared by the methods shown in the following reaction schemes A, B, and C wherein $R^2$, Y, and $R^6$ are defined above, unless otherwise indicated. As will be evident to those skilled in the art and as demonstrated in the examples, reactive groups such as amino, hydroxy, carboxy, etc. may be protected by standard methods and subsequently deprotected when it is appropriate.

REACTION SCHEME A
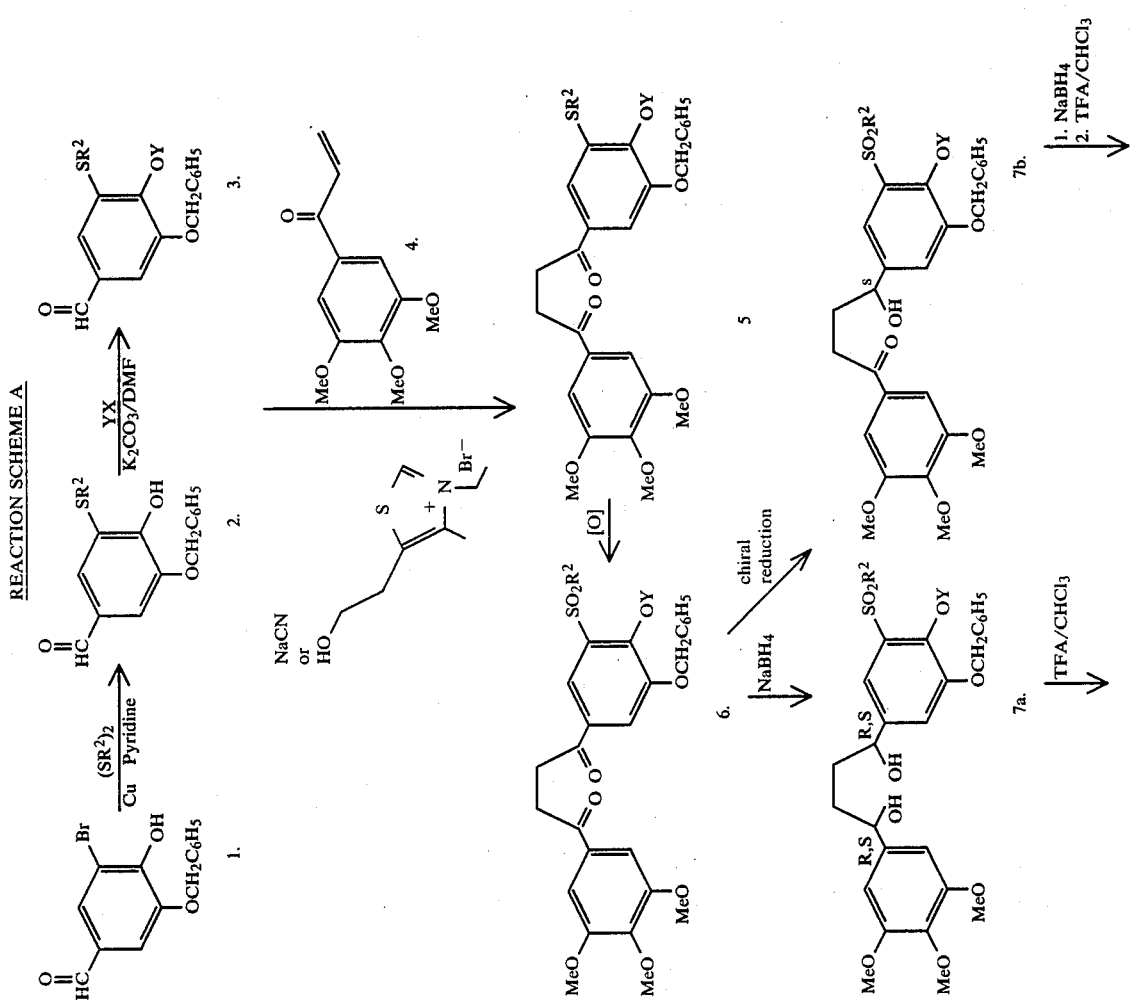

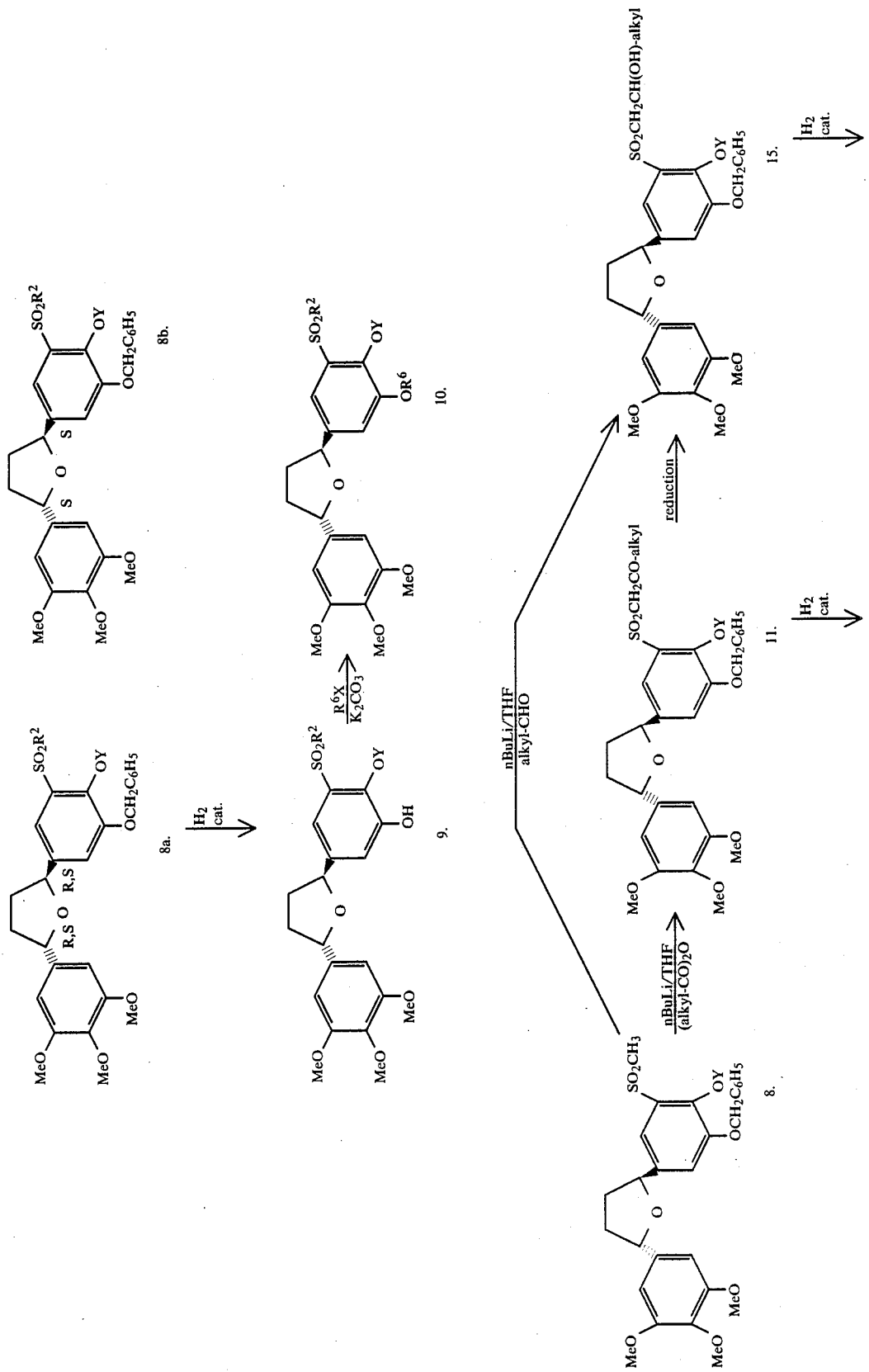
-continued
REACTION SCHEME A

-continued
REACTION SCHEME A
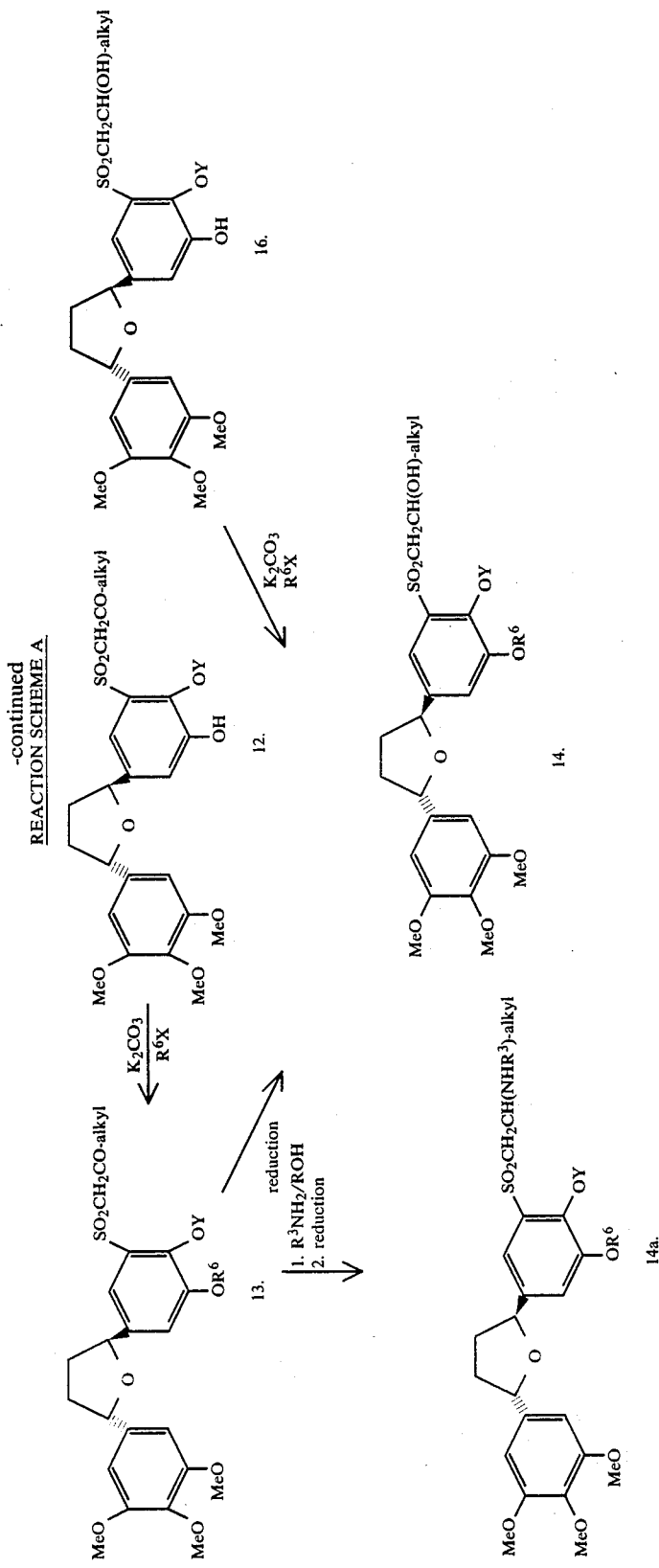

REACTION SCHEME B
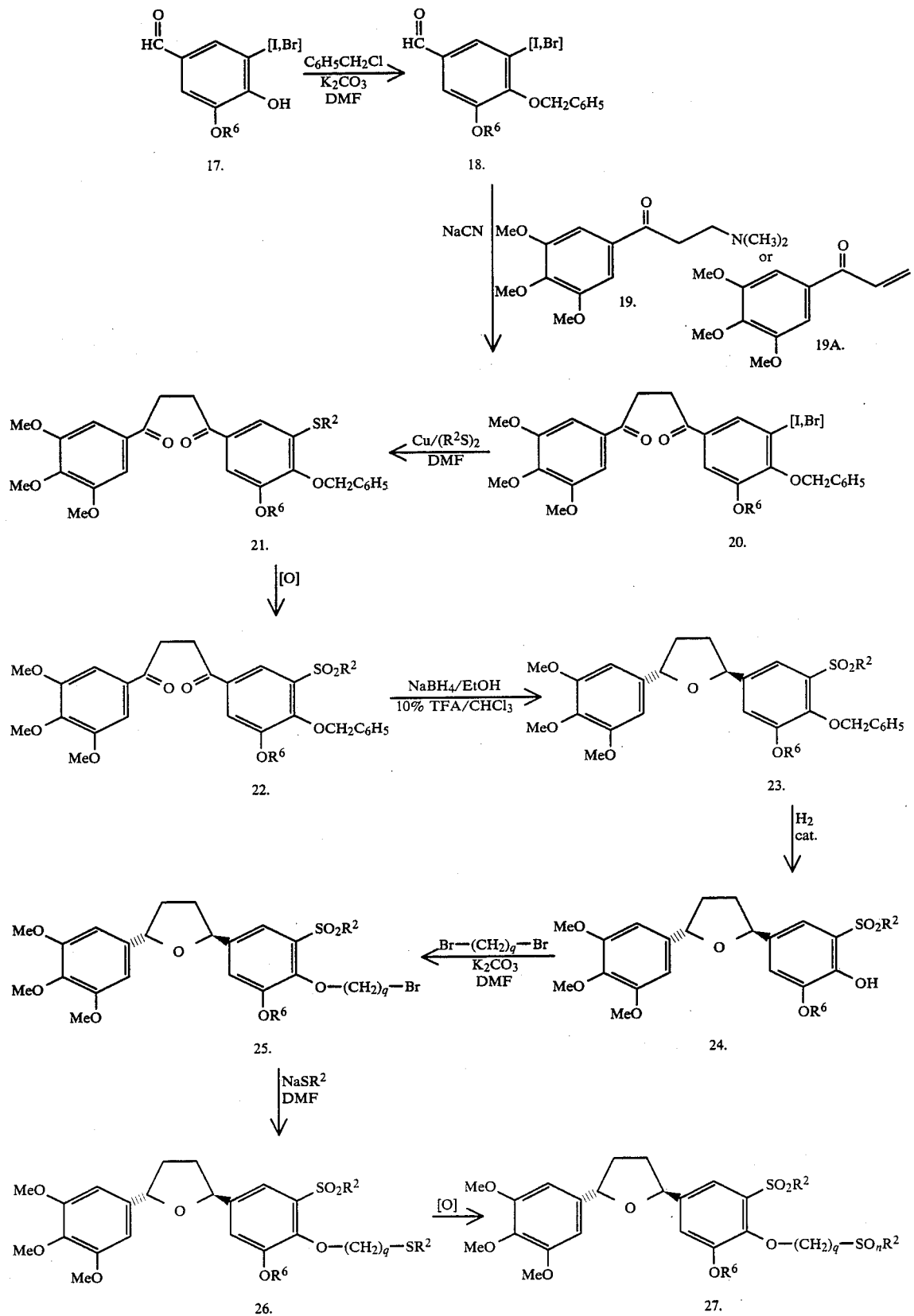

REACTION SCHEME C

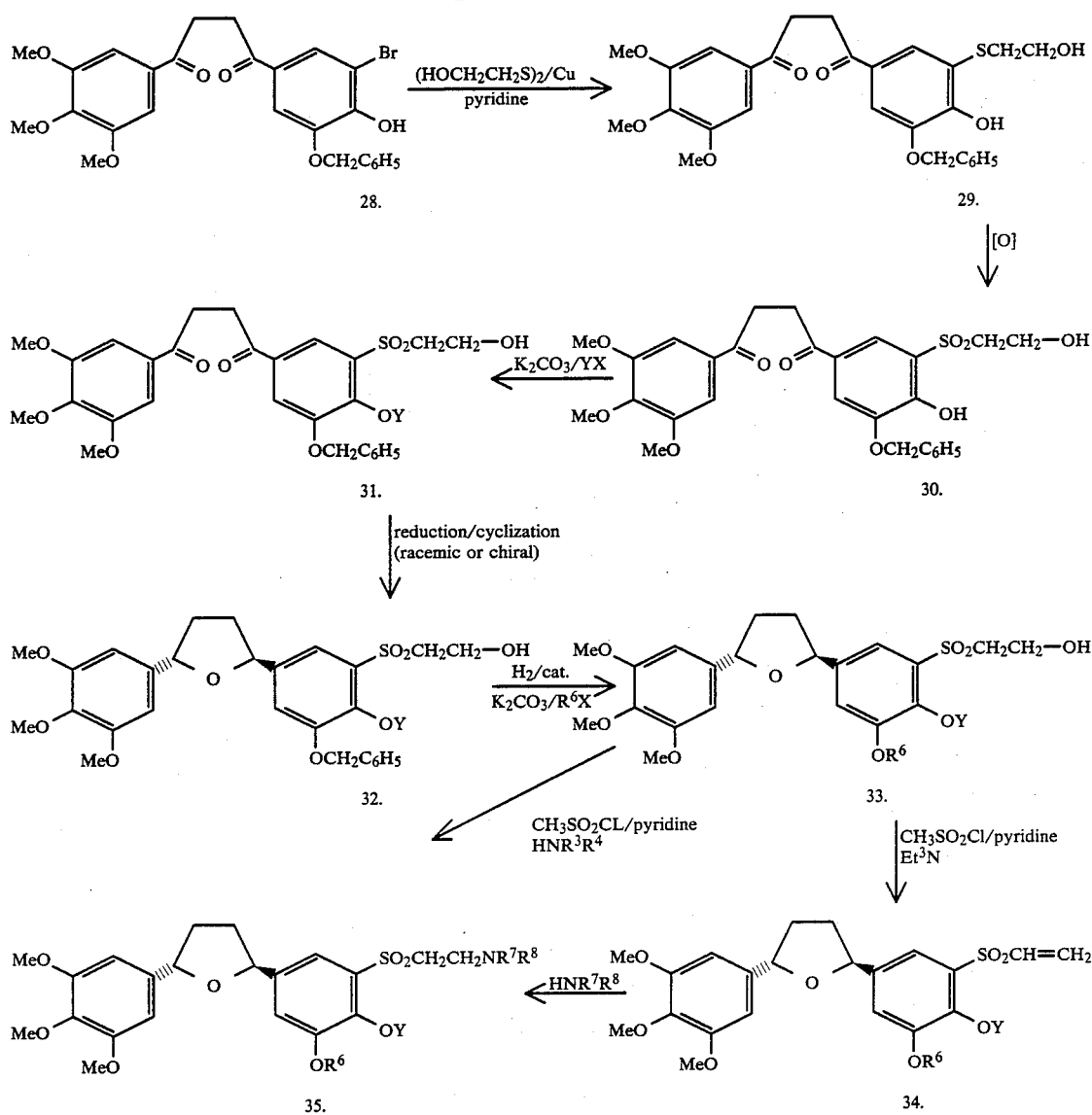

Scheme A

The compounds of formula (1) may be prepared according to a sequence beginning with 5-benzyloxy-3-bromo-4-hydroxybenzaldehyde 1 which can be prepared according to the procedures outlined by J. Thiem [J. Chem. Soc. Perkin I, 1186–1190 (1977)]. This compound is reacted with the appropriate disulfide $(SR^2)_2$ and copper powder in pyridine at elevated temperatures to provide compound 2. The 4-position may then be derivatized by alkylation with the appropriate alkylhalide, mesylate, or tosylate Y-X, using a base such as $K_2CO_3$ in a suitable solvent such as N,N-dimethylformamide (DMF) or tetrahydrofuran (THF) to provide compound 3. Alternatively, it is possible to prepare compound 3 by reversing the order of the last two steps. One of several alternative approaches to preparing diketone 5 is by reacting aldehyde 3 with vinylketone 4 and a base such as triethylamine with a catalytic amount of cyanide ion in DMF or 3-ethyl-5-(2-hydroxyethyl)-4-methylthiazolium bromide in DMF. Vinylketone 4 may be prepared from 3,4,5-trimethoxyacetophenone via conversion to a Mannich base, quaternization and elimination by standard procedures. Oxidation of the sulfide group of compound 5 with an oxidizing agent such as m-chloroperoxybenzoic acid (mCPBA) in methylene chloride ($CH_2Cl_2$) provides sulfone 6.

Furan 8a is prepared via reduction of diketone 6 with reducing agents such as sodium borohydride ($NaBH_4$) in a mixture of THF and methanol ($CH_3OH$) at 0° C., or lithium aluminum hydride ($LiAlH_4$) in diethylether or THF. Alternative methods include catalytic reduction using hydrogen and catalysts such as palladium, platinum, or rhodium. The resulting diol 7a is dissolved in chloroform ($CHCl_3$) and carefully reacted with a dilute solution of trifluoroacetic acid (TFA) in $CHCl_3$ at 0° C. If adequate care is taken with this reaction the trans-furan 8a is produced as the major product and can be separated from the cis diastereomer by chromatography on silica gel normally eluting with a mixture of hexanes and ethyl acetate. Alternative methods of furan formation from 7a include such reagents as methanesulfonyl chloride triethylamine or triphenylphosphine dibromide. The desired trans isomer 8a is usually a less polar material than the cis isomer on silica gel. The usually preferred chiral (−)-(S,S)-enantiomer may be prepared from diketone 6 by the specific reduction to hydroxyketone 7b using a bulky reducing agent such as lithiumtri-t-butoxyaluminumhydride [LiAlH(OtBu)$_3$], or controlled reduction with NaBH$_4$. Hydroxyketone 7b can be chemically resolved via the its mandelate esters to provide chiral (S)-hydroxyketone 7b. Alternatively, compound 7b can be prepared in the chiral (S) form by using a chiral reducing agent such as the lithiumaluminumhydride-(S)-(−)-1,1'-bi-2-naphthol complex in THF normally at −78° C. chiral trans furan 8b is prepared by sequential reduction of the remaining carbonyl-group with NaBH$_4$ and cyclization with TFA as for compound 8a the 5'-position is then derivatized by removal of the benzyl protecting group by standard deprotection methods such as hydrogenation using a catalyst such as palladium on carbon in a solvent such as ethanol (EtOH) or ethyl acetate. The free phenol may then be alkylated with the appropriate alkylating agent $R^6X$ where X is a halide, mesylate or tosylate and a base such as $K_2CO_3$ in DMF, EtOH or another suitable solvent.

A variant of Scheme A is the further elaboration of compound 8a or 8b where $R^2$ is methyl. This compound may be acylated with by reaction with n-butyllithium in THF at −78° C. followed by an ester, acid chloride or anhydride such as ethyl acetate acetylchloride or acetic anhydride to give ketosulfone 11 which can be further elaborated into compound 13 by procedures previously outlined. A further elaboration is to reduce ketosulfone 13 to hydroxysulfone 14 using a reducing agent such as NaBH$_4$ in L to H or THF and CH$_3$OH. Alternatively, compound 11 can be similarly reduced to hydroxysulfone 15 which can then be deprotected and alkylated to give 14. Alternatively, hydroxysulfone 15 can be produced directly from compound 8 by reaction with the appropriate aldehyde after reacting 8a or 8b with n-Butyllithium or a similar base.

Other elaborations at position 3' may be carried out starting with compound 8a or 8b ($R^2$=CH$_3$, Ethyl, etc.) by procedures analogous to those described herein.

A further series of amino compounds 14a can be prepared from ketosulfone 13 or 15 by reacting them hydroxylamine or substituted amines $R^3NH_2$ in an alcoholic solvent such as ethanol (ETOH) to obtain oximes or imines. These imines or oximes may then be reduced to free or substituted amines 14a employing reducing agents such as sodium borohydride, sodium cyanoborohydride in ETOH or by catalytic hydrogenation by methods previously described.

Scheme B

Scheme B is an alternative route to compounds of formula I which may be preferred for some compounds, in particular, those with elaborate Y-substituents such as Y=(CH$_2$)$_q$-SR$^1$, etc. Process B is similar to process A accept that one begins with compound 17 where $R^6$ is already attached such as 5-iodovanillin ($R^6$=CH$_3$) or other compounds. The 4-position of compound 17 is protected as the benzyl ether by standard procedures to give compound 18 which can be elaborated into racemic trans or chiral trans furans 23 by methods outlined for Process A. Furan 23 may be deprotected and elaborated as outlined for $R^6$ in Process A. An example shown here involves the alkylation of phenol 24 with a dibromoalkane such as dibromoethane in DMF with $K_2CO_3$ to give 25 (Y=—(CH$_2$)$_2$-Br). Compound 25 may be further reacted with nucleophiles such as the sodium or potassium salts of substituted or unsubstituted arylthiols such as thiophenol. The sodium salts can be prepared by reacting the thiol compound in THF or DMF with sodium hydride (NaH). To this reaction mixture at room temperature is then added bromide 25 to give product 26. Sulfide 26 can be further elaborated to sulfone 27 by oxidation with mCPBA in CHCl$_3$.

Scheme C: 3'-(2-aminoethyl)sulfone analogs (34)

A series of substituted or unsubstituted 2-aminoethylsulfonyl analogs 25 may be prepared by the scheme outlined in Scheme C. 2-hydroxyethylsulfone compounds 33 can be prepared by methods previously described and can then be derivatized as their tosylates or methanesulfonates by methods known to those in the art. Alternatively, the hydroxy group may be converted to a halide such as bromo, by one of a variety of commonly used methods such as triphenylphosphine and N-bromosuccinimide, or carbon tetrabromide or by phosphorous tribromide, elimination to vinylsulfone 34 may be achieved by reacting the bromide, tosylate, or mesylate with a tertiary amine such as triethylamine. The vinyl sulfone 34 may then be reacted with an amine R$^7$R$^8$NH (wherein R$^7$R$^8$ NH is a mono or dialkyl amino group) in a solvent such as acetonitrile producing aminoethylsulfones 35. Compounds of structure 35 may also be prepared from the precurser mesylates, etc. by reacting them directly with amines R$^7$R$^8$NH.

This invention also relates to a method of treatment for patients (or mammalian animals raised in the dairy, meat, or fur industries or as pets) suffering from disorders or diseases which can be attributed to PAF as previously described, and more specifically, a method of treatment involving the administration of the PAF antagonists of formula (I) as the active constituents.

Accordingly, the compounds of formula (I) can be used among other things to reduce pain and inflammation, to correct respiratory, cardiovascular, and intravascular alterations or disorders, and to regulate the activation or coagulation of platelets, to correct hypotension during shock, the pathogenesis of immune complex deposition and smooth muscle contractions.

For the treatment of inflammation such as rhumatoid arthritis, osteoarthritis, and eye inflammation, cardio vascular disorder, asthma, shock syndrome or other diseases mediated by the PAF, the compounds of formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The Oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents may also be present.

The pharmaceutical compositions of the invention may also be in the form of oil-in water emulsions. The oily phase may be a vegetable oil, for example olive oil or arachis oil, or a mineral oil, for example liquid paraffin or mixtures of these. Suitable emulsifying agents may be naturally occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, Jellies, solutions or suspensions, etc., containing the compounds of Formula (I) are employed.

Dosage levels of the order of from about 0.05 mg to about 140 mg per kilogram of body weight per day are useful in the treatment of the above-indicated conditions (about 2.5 mg to about 7 gms. per patient per day). For example, inflammation may be effectively treated by the administration of from about 0.01 to 50 mg of the compound per kilogram of body weight per day (about 0.5 mg to about 3.5 gms per patient per day).

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

A representative number of compounds of the instant invention of the formula (I) exhibit in vitro antagonistic activities with respect to PAF:

The compounds of formula (I) inhibit PAF-induced functions in both the cellular and tissue levels by changing the PAF binding to its specific receptor site. The ability of a compound of formula (I) to inhibit the PAF binding to its specific receptor binding site on rabbit or human platelet or PMN plasma membranes was measured by a recently developed assay.

The inhibition of $^3[H]$ PAF or $^3[H]$N-methylcarbamoyl-PAF binding to the human or rabbit platelet or PMN plasma membrane by a PAF antagonist of formula (I) was determined by a method employing isotopic labeling and filtration techniques. Generally, a series of Tris-buffered solutions of the selected antagonist at predetermined concentrations were prepared. Each of these solutions contains 1 pmole of $^3$H-PAF, a known amount of the test antagonist, and a sufficient amount of the pH 7.5 Tris-buffer solution (10 mM Tris, 0.25% bovine serum albumin, and 150 mM NaCl per ml water) to make the final volume of 1 ml. After adding into a set of test tubes each with 100 μg of the platelet plasma membrane suspension (S. B. Hwang, et al., *Biochemistry*, Vol. 22, pp. 4756–4763, 1983) and one of the Tris-buffer solutions described above, the resulting mixture in each test tube was incubated at 0° C. for about one hour or until the reaction was complete. Two control samples, one of which ($C_1$) contains all the ingredients described above except the antagonist and the other ($C_2$) contains $C_1$ plus a 1000-fold excess of unlabeled PAF, were also prepared and incubated simultaneously with the test samples. After the incubation was completed, the contents of each test tube were filtered in vacuo through a Whatman GF/C fiberglass filter and the residue washed rapidly several times with a total of 20 ml cold (0°–5° C.) Tris-buffer solution. Each washed residue was then suspended in 10 ml scintillation solution (Aquasol 2, New England Nuclear, Connecticut) and the radioactivity was counted in a Packard Tri-Carb 460CD Liquid Scintillation System. Defining the counts from a test sample as "Total binding with antagonist"; the counts from the control sample $C_1$, as "Total binding $C_1$"; and the counts from the control sample $C_2$ as "non-specific binding $C_2$", the percent inhibition of each test antagonist can be determined by the following equations:

$$\% \text{ Inhibition} = \frac{(\text{Total binding } C_1) - \text{Total binding with antagonist} \times 100}{\text{Specific binding}}$$

Specific binding = (Total binding $C_1$) − (non-specific binding $C_2$)

in vitro PAF-induced platelet aggregation (rabbit or human platelets); PAF-induced guinea pig peritoneal PMN (polymorphonuclear leukocytes) aggregation; PAF-induced human PMN secretion; and PAF induced guinea pig smooth muscle contraction although they are not $H_2$-receptor antagonists. They are also shown in these inhibition studies to be highly specific to PAF. For example, they do not inhibit the binding of $H_1$ antagonist ($^3$H-pyrilamine) to guinea pig brain membrane, nor do they inhibit the binding of a cholecystokinin (CCK) receptor based on an assay on isolated rat pancreas membrane. Furthermore, they affect no or only minute inhibition on the histamine-induced ileum contraction from guinea pigs.

The antagonistic activity of representative compounds of structural formula (I) in the transconfiguration is summarized in the following table I:

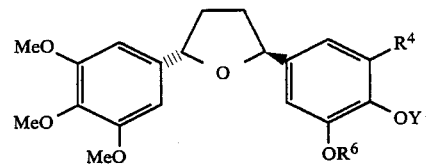

| $R^4$ | Y | $R^6$ | % inhibitor* |
|---|---|---|---|
| $SO_2CH_2COCH_3$ | $-CH_2CH_2CH_3$ | $-(CH_2)_3-N(CH_3)_2$ | 17 |
| $SO_2CH_2COCH_3$ | $-CH_2CH_2CH_3$ | $-(CH_2)_3-OH$ | 66 |
| $SO_2CH_2COCH_3$ (2S,5S) | $-CH_2CH_2CH_3$ | $-(CH_2)_3-OH$ | |
| $SO_2CH_2COCH_3$ | $-CH_2CH_2CH_3$ | $-(CH_2)_3-O-PO_3H_2$ | |
| $SO_2CH_2COCH_3$ (2S,5S) | $-CH_2CH_2CH_3$ | $-(CH_2)_3-O-PO_3H_2$ | |
| $SO_2CH_2COCH_3$ | $-CH_2CH_2CH_3$ | $-CH_2COCH_3$ | 65 |
| $SO_2CH_2CH(OH)CH_3$ | $-CH_2CH_2CH$ | $-(CH_2)_3-OH$ | 26 |
| $SO_2CH_2CH(OH)CH_3$ | $-CH_2CH_2CH_3$ | $-CH_2COCH_3$ | 52 |
| $SO_2CH_2CH(NH_2)CH_3$ | $-CH_2CH_2CH_3$ | $-(CH_2)_3-OH$ | 18 |
| $SO_2CH_2CH(NHCH_3)CH_3$ | $-CH_2CH_2CH_3$ | $-(CH_2)_3-OH$ | 38 |
| $SO_2CH_2CH[N(CH_3)_2]CH_3$ | $-CH_2CH_2CH_3$ | $-(CH_2)_3-OH$ | 23 |
| $SO_2CH_2CH(NHCH_2CH_3)CH_3$ | $-CH_2CH_2CH_3$ | $-(CH_2)_3-OH$ | 36 |
| $SO_2CH_2CH_2NHCH_3$ | $-CH_2CH_2CH_3$ | $-CH_2CH_2CH_3$ | 58 |
| $SO_2CH_2CH_2N(CH_3)_2$ | $-CH_2CH_2CH_3$ | $-CH_2CH_2CH_3$ | 58 |
| $SO_2CH_2CH_2NH_2$ | $-CH_2CH_2CH_3$ | $-CH_2CH_2CH_3$ | 27 |
| $SO_2CH_2CH_2NHCH_2CH_3$ | $-CH_2CH_2CH_3$ | $-CH_2CH_2CH_3$ | 42 |
| $SO_2CH_2CH_2NH$-n-propyl | $-CH_2CH_2CH_3$ | $-CH_2CH_2CH_3$ | 33 |
| $SO_2CH_2CH_2N(CH_3)_2$ | $-CH_2CH_2CH_3$ | $-(CH_2)_3-OH$ | 46 |
| $SO_2CH_2CH_2N(CH_3)_2$ | $-CH_2CH_2CH_3$ | $-CH_2COCH_3$ | 31 |
| $SO_2CH_2CH_2-OH$ | $-CH_2CH_2CH_3$ | $-CH_2COCH_3$ | 33 |

-continued

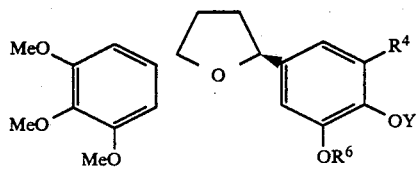

| R⁴ | Y | R⁶ | % inhibitor* |
|---|---|---|---|
| SO₂CH₂CH₂N(CH₃)₂ | —CH₂CH₂CH₃ | —(CH₂CH(OH)CH₃ | 14 |

*% inhibition of the binding of [3H] N-methylcarbamoyl-PAF to human platelet membranes at a drug concentration of 3%

The following examples illustrate the preparation of representative compounds of this invention and pharmaceutical compositions thereof and as such are not to be considered as limiting the invention set forth in the claims appended hereto.

EXAMPLE 1

2-[3-(2-Oxopropylsulfonyl)4-n-propoxy-5-{3-(N,N-dimethylamino)-n-propoxy}phenyl]-5-(3,4,5-trimethoxyphenyl)tetrahydrofuran Step 1A: 3-Methylthio-4-hydroxy-5-benzyloxybenzaldehyde A five liter flask equipped with a mechanical stirrer was charged with 100 g of 3-Bromo-4-hydroxy-5-benzyloxybenzaldehyde 80 g Cu powder, 80 mL methyldisulfide and 5 L pyridine, and the mixture was heated at 90° C. overnight with gentle stirring. The following day, the reaction mixture was filtered and most of the pyridine (1.3 L) was distilled off. The remaining solid residue was washed with about 2 L of methylene chloride and combined with the residue left after pyridine evaporation. The combined organic fraction was washed with 1.5N HCl until the dark methylene chloride layer turned light brown and the aqueous layer was clear. The resulting light brown methylene chloride layer was dried over MgSO₄ and filtered through a bed of silica gel. Evaporation and crystallization from methylene chloride-hexane gave the title compound: NMR(200 MHz, CDCl₃) δ 2.50 (t, SCH₃), 5.20(s, OCH₂Ar), 6.72(s, OH), 7.34–7.46(m, ArH), 9.78(s, ArCHO).

In an alternative procedure a 50-L flask equipped with a mechanical stirrer was charged with 3-bromo-4-hydroxy-5-benzyloxybenzaldehyde (1.332 kg, 4.34 mol), Copper powder (1.068 kg, 16.82 mol), dimethyldisulfide (1.068 kg, 11.36 mol) and pyridine (23 L). The mixture was heated at 95° C. overnight with gentle stirring, filtered, and the filtered cake was washed with dichloromethane (30 L). The pyridine filtrate was distilled off to leave a black residue, from which the product was extracted with the dichloromethane washes. The combined organic extracts were washed with 2N HCl until it became light brown and the acidic aqueous layer was clear. The organic layer was dried (MgSO₄), filtered, and the filtrate was evaporated to dryness. Crystallization from dichloromethane-hexane gave the title compound (900 g, 76%): mp 117°–119° C.; NMR (CDCl₃) δ 2.50 (s, SCH₃), 5.20 (s, OCH₂Ar), 6.72 (s, OH), 7.34–7.46 (m, ArH), 9.78 (s, ArCHO)

3-bromo-4-hydroxy-5-benzyloxybenzaldehyde

As appreciated by those of skill in the art, starting material for the above captioned alternative procedure may be prepared as follows. 3-bromo-4-hydroxy-5-benzyloxybenzaldehyde (932 g, 4.08 moles) [from 3,4-dihydroxybenzaldehyde; J. Chem. Soc. Perkin I, 1186 (1977)] was dissolved in acetic acid (7.46 l) with stirring and warmed to 45°–50° C. Sodium acetate (373 g) was added and when the mixture was cooled to 30° C., bromine (233 ml, 4.5 mole) in acetic acid (932 ml) was added with rapid drip over 1.5 hours. A light colored precipitate forms shortly after addition begins. After the addition was complete, the mixture was stirred for 45 minutes, water (1875 ml) was added, and then stirred for 15 minutes. The precipitate was filtered, air dried and washed with water and then hexane (8l.). The residue was then dried at 40° C. overnight under high vacuum yielding 1.3 kg of the title compound. m.p. 160°–162° C. A second 1.74 kg run yielded the desired product.

STEP 1B: 3-Methylthio-4-n-propoxy-5-benzyloxybenzaldehyde 64.5 g of 3-methylthio-5-benzyloxy-4-hydroxybenzaldehyde dissolved in a 75 mL of DMF was treated with 50 g of K₂CO₃ and 32 g of 1-bromopropane and stirred overnight at 70° C. The next day about 1.5 liters of methylene chloride and an equal amount of water was added to the reaction mixture. The organic layer was removed, washed three times with distilled water, dried over MgSO₄ and evaporated to yield the title compound as viscous liquid that solidified slowly: NMR(200 MHz, CDCl₃) δ 1.02(t, CH₂CH₂CH₃), 1.82(m, CH₂CH₂CH₃), 2.48(s, SCH₃), 4.12 (t, OCH₂CH₂CH₃), 5.18(s, OCH₂Ar), 7.26–7.52(m, ArH), 9.86(s, ArCHO).

STEP 1C: 1-(3-Methylthio-4-propoxy-5-benzyloxyphenyl)4-(3,4,5-trimethoxyphenyl)butan-1,4-dione 175 g 3-methylthio-4-n-propoxy-5-benzyloxybenzaldehyde, 135 g of 3,4,5-trimethoxyphenylvinylketone, 10 g of 3-ethyl-5-(2-hydroxyethyl)-4-methylthiazoliumbromide, 25 mL of triethyl amine dissolved in 150 ml of dimethylformamide was heated at 60° C. overnight, and the reaction mixture was treated with 400 mL of 1.5N HCl and the aqueous layer decanted. The residue was treated again with fresh 400 mL of 1.5N HCl and decanted two more times. The remaining residue was crystallized from 400 mL of methanol and washed thoroughly with methanol, hexane, and methanol and dried to yield the title compound as a tan solid: NMR(200 MHz, CDCl₃) δ 1.03(t, CH₂CH₂CH₃), 1.82(m, CH₂CH₂CH₃), 2.50(s, SCH₃), 3.43(s, C(O)CH₂CH₂CO, 3.94(s, 3 OCH₃), 4.11 (t, OCH₂CH₂CH₃), 5.17(s, OCH₂Ar), 7.30–7.52(m, ArH).

1-(3,4,5-Trimethoxyphenyl)prop-2-en-1-one

Concentrated hydrochloric acid (1 mL) was added to a stirred mixture of 3,4,5-trimethoxyacetophenone (210 g, 1 mol), dimethylamine hydrochloride (81 g, 1 mol) and paraformaldehyde (45 g, 1.5 mol) in ethanol (300 mL). The reaction mixture was heated under reflux for 1 hour. Another portion of paraformaldehyde (30 g, 1 mol) was added and the heating was continued for another 2 hours. The warm reaction mixture was poured with vigorous stirring into acetone (2.4 L). The slurry was heated at 60° C. for 15 minutes, cooled, and filtered. The solid was washed with acetone and dried to provide the hydrochloride salt of 3-(N,N-dimethylamino)-1-(3,4,5-trimethoxyphenyl)propan-1-one (196 g, 65%): $Rf$0.05 (SiO$_2$; hexane-ethyl acetate, 2:1; v/v); mp 175° C. A mixture of the above hydrochloride (147.5 g, 0.48 mol) in 1N NaOH (750 mL) was shaken with ethyl acetate (4×100 mL). The combined organic extracts were washed with brine, dried, and evaporated in vacuo to give 3-(N,N-dimethylamino)-1-(3,4,5-trimethoxyphenyl)propan-1 one mp 45°-47° C.

A solution of the above compound (242.5 g, 0.91 mol) in ethyl ether (1.62 L) was reacted under nitrogen with methyl iodide (83 mL, 1.27 mol) at room temperature for 2 h. The solid was filtered and dried under high vacuum overnight at room temperature to provide 3-(N,N,N-trimethylammonio)-1-(3,4,5-trimethoxyphenyl)propan-1-one iodide which was used directly in the following experiment without further purification.

The above iodide (355.9 g, 0.87 mol) was suspended in a mixture of water (3.56 L) and ethyl acetate (2.54 L) and heated under reflux with rapid stirring for 2-3 hours. The mixture was cooled and the pale yellow organic layer was removed. Fresh ethyl acetate (2 L) was added and the mixture was again heated under reflux for 1 hour and the process was repeated once again. The organic extracts were combined, washed with brine, dried (MgSO$_4$), and evaporated to a yellow oil which was crystallized from hexane-ethyl ether to give 1-(3,4,5-trimethoxyphenyl)prop-2-en-1-one: mp 46°-47° C.; NMR (CDCl$_3$) δ 3.94 (s, 3 OCH$_3$), 5.92 (2 d, J=1.5 & 9.0 Hz, CH=CH$_2$), 6.44 (2 d, J=1.5 & 16 Hz, CH=CH$_2$), 7.18 (2 d, J=9.0 & 16 Hz, CH=CH$_2$), 7.28 (ArH).

STEP 1D: 1-(3-Methylsulfonyl-4-n-propoxy-5-benzyloxyphenyl)-4-(3,4,5-trimethoxyphenyl)butan-1,4-dione 21.2 g of 1-(3-methylthio 4-propoxy-5-benzyloxyphenyl)-4-(3,4,5-trimethoxyphenyl) butan-1,4-dione dissolved in 350 mL of methylene chloride was cooled in ice bath and treated with 16 g of mCPBA (80%) in small portions. After 2-3 h of stirring, the mixture was cooled to 0° C., filtered to remove 3-chlorobenzoic acid and evaporated to a small volume The residue obtained as such was taken up in ethyl acetate, washed with aqueous NaOH, water, brine, dried over MgSO$_4$ and evaporated. The residue was crystallized from methanol to yield the title compound NMR(200 MHz, CDCl$_3$) δ 0.99(t, CH$_2$CH$_2$CH$_3$), 1.85 (m, CH$_2$CH$_2$CH$_3$), 3.30(s, SO$_2$CH$_3$), 3.45 (s, C(O)CH$_2$CH$_2$CO, 3.93(s, 3 OCH$_3$), 4.26 (t, OCH$_2$CH$_2$CH$_3$), 5.20(s, OCH$_2$Ar), 7.29 (s, 4-ArH), 7.36-7.48(m, ArH), 7.92 & 8.25(2 d, 1H each, 1-ArH).

STEP 1E: (−) (1S)-1-(3-Methylsulfonyl-4-n-propoxy-5-benzyloxyphenyl)-4-(3,4,5-trimethoxyphenyl)butan-1-ol-4-one A solution of 4.1 mL ethanol in 41 mL of THF was added dropwise to a stirred solution of 69 mL of 1N lithium aluminum hydride in tetrahydrofuran. After 15 min, a solution of 20.06 g of (S)-(−)-binaphthol in 180 mL of THF was added dropwise over a period of 2 h while maintaining the temperature of the milky mixture below 30° C. After stirring for additional 30 min at room temperature, the reaction mixture was cooled to −78° C., and a solution of 16 g of 1-(3-methylsulfonyl 4-n propoxy-5-benzyloxyphenyl)-4-(3,4,5-trimethoxyphenyl)butan-1,4-dione in 125 mL THF was added dropwise to the mixture over a period of 1 h and stirring continued for 1-1.5 h. The reaction mixture was quenched with 28 mL of methanol and then concentrated in vacuo to remove THF and methanol. The residue was taken up in ethyl acetate and the organic phase was washed with 1N HCl, water, brine and concentrated in vacuo. Most of the (−)-binaphthol (14.2 g) was precipitated with methylene chloride/hexane.

The procedure described in the preceding paragraph was repeated with another 16 g of 1-(3-methylsulfonyl-4-n-propoxy-5-benzyloxyphenyl)-4-(3,4,5-trimethoxyphenyl)butan 1,4-dione, and the concentrated filtrates obtained after precipitation of (−)-binaphthol were combined, chromatographed on silica column (hexane/ethyl acetate), and crystallized from methylene chloride-hexane to yield the title compound as a glassy solid: [α]$_D$-10.1°: NMR(200 MHz, CDCl$_3$) δ 0.98(t, CH$_2$CH$_2$CH$_3$), 1.82(m, CH$_2$CH$_2$CH$_3$), 2.04-2.24(m, CH$_2$CHOH), 3.10(t, C(O)CH$_2$CH$_2$CHOH, 3.26(s, SO$_2$CH$_3$), 94(s, 3 OCH$_3$), 4.16(t, OCH$_2$CH$_2$CH$_3$), 4.85 (m, CH$_2$CHOH), 5.16(s, OCH$_2$Ar), 7.23(s, 4-ArH), 7.30-7.52(m, ArH).

STEP 1F: (−)-(1S)-1-(3-Methylsulfonyl-4-n-propoxy-5-benzyloxyphenyl)-4-(3,4,5-trimethoxyphenyl)butan-1.4-diol 35 g of (−)-(1S)-1-(3-methylsulfonyl-4-n-propoxy-5-benzyloxyphenyl)-4-(3,4,5-trimethoxyphenyl)butan-1-ol-4-one dissolved in a mixture of 300 mL dry THF and 100 mL of methanol was treated with 3.5 g of NaBH$_4$ at 0° C. and stirred for 3 h. The reaction mixture was then allowed to gradually warm to room temperature and stirring was continued for additional 2 h. After the completion of the reaction, the solvent was evaporated at reduced pressure and the residue obtained as such was redissolved in 300 ml of ethyl acetate. The organic layer was washed with 1.5N HCl, distilled water and brine respectively, and then dried over MgSO$_4$ and evaporated to yield a colorless syrup which was used without further purification.

STEP 1G: 1-(3-Methylsulfonyl-4-n-propoxy-5-benzyloxyphenyl)-4-(3,4,5-trimethoxyphenyl)butan-1,4-diol This compound was prepared from 1-(3-methylsulfonyl-4-n-propoxy-5-benzyloxyphenyl)-4-(3,4,5-trimethoxy- phenyl)butan-1,4-dione as shown for (−)-(1S)-1-(3-methylsulfonyl-4-n-propoxy-5-benzyloxy phenyl)-4-(3,4,5-trimethoxyphenyl) butan-1-ol-4-one and used without further purification.

STEP 1H: (−)-trans-(2S,5S)-2-(3-Methylsulfonyl-4-n-propoxy-5-benzyloxyphenyl)-5-(3,4,5-trimethoxyphenyl) tetrahydrofuran 37 g of (−)-(1S)-1-(3-methylsulfonyl-4-n-propoxy-5-benzyloxy- phenyl)-4-(3,4,5-trimethoxyphenyl) butan-1,4-diol dissolved in 185 mL of chloroform (stabilized with ethanol) was treated dropwise with 10% TFA in chloroform and stirred for h at 0° C.. The reaction mixture was washed with 5% NaOH, water, brine, dried over MgSO$_4$ and evaporated to a colorless syrup. It was then separated on a silica column (30% ethyl acetate in hexane) into cis and trans isomers. The trans isomer was crystallized from ether: [a]$_D$-62.4.; NMR(200 MHz, CDCl$_3$) δ98 (t, CH$_2$CH$_2$CH$_3$), 1.82(m, CH$_2$CH$_2$CH$_3$), 1.9-2.6(m, 3-CH$_2$ & 4-CH$_2$), 3.27(s, SO$_2$CH$_3$), 3.85(s, OCH$_3$), 3.94(s, 2 OCH$_3$), 4.16(t, OCH$_2$CH$_2$CH$_3$), 5.17(s, OCH$_2$Ar), 5.06–5.28(m, 2-CH & 5-CH), 6.61(s, 5-ArH), 7.28–7.54(m, ArH).

STEP 1I: racemic trans-2-(3-Methylsulfonyl-4-n-propoxy-5-benzyloxyphenyl)-5-(3,4,5-trimethoxyphenyl)tetrahydro-furan This compound was prepared from 1-(3-methylsulfonyl-4-n-propoxyphenyl)-4-(3,4,5-trimethoxy-5-benzyloxyphenyl)butan-1,4-diol by procedures described in Example 1, Step H.

STEP 1J: trans-2-[3-(2-oxopropylsulfonyl)-4-n-propoxy-5-benzyloxyphenyl]5-(3,4,5-trimethoxyphenyl)tetrahydro-furan 2.7 g trans-2-(3-methylsulfonyl-4-n-propoxy-5-benzyloxyphenyl)-5-(3,4,5-trimethoxyphenyl)tetrahydrofuran dissolved in 15 mL THF was cooled to 78° and treated with 5.3 mL of 1.6M n-BuLi. After about 5 minutes of stirring, to the resulting dark solution, 1.0 mL of acetic anhydride was added. The yellow reaction mixture was allowed to warm up to room temperature and treated with 3–4 g of solid ammonium chloride, water and ether. The ether layer was separated, dried over NaSO$_4$, evaporated and chromatographed over silica (20% ethyl acetate in hexane) to yield the title compound after crystallization from ether: NMR (200 MHz, CDCl$_3$) δ0.98 (t, CH$_2$CH$_2$CH$_3$), 1.83 (m, CH$_2$CH$_2$CH$_3$), 1.9–2.6 (m, 3-CH$_2$ & 4-CH$_2$), 2.38 (s, CH$_3$C(O)CH$_2$), 3.86 (s, OCH$_3$), 3.88 (s, 2 OCH$_3$), 4.18 (t, OCH$_2$CH$_2$CH$_3$), 4.48 (s, CH$_3$C(O)CH$_2$), 5.18 (s, OCH$_2$Ar), 5.06–5.28 (m, 2-CH & 5-CH), 6.61 (s, 5-ArH), 7.32–7.54 (m, ArH).

STEP 1K: (−)-trans-(2S,5S)-2-[3-(2-Oxopropylsulfonyl)-4-n-propoxy-5-benzyloxyphenyl]-5-(3,4,5-trimethoxyphenyl)tetrahydrofuran This compound was prepared from (−)-trans(2S,5S)-2-(3-methylsulfonyl-4-n-propoxy-5-benzyloxyphenyl)-5-(3,4,5-trimethoxyphenyl)tetrahydrofuran as shown in the racemic case STEP J.

STEP 1L: 2-[3-(2-Oxopropylsulfonyl)-4-n-propoxy 5-hydroxyphenyl]-5-(3,4,5-trimethoxyphenyl)tetrahydro-furan A mixture of 1.2 g of 2-[3-(2-oxopropylsufonyl)-4-n-propoxy-5-benzyloxy- phenyl]-5-(3,4,5-trimethoxyphenyl) tetrahydrofuran, 400 mg 10% Pd/C, 1–2 drops of acetic acid in 100 mL of ethyl acetate was stirred under H$_2$ at 40 psi for 45 minutes. The reaction mixture was filtered over a bed of celite and evaporated in vacuo to yield the title compound: NMR(200 MHz, CDCl$_3$) δ 1.10 (t, CH$_2$CH$_2$CH$_3$), 1.92 (m, CH$_2$CH$_2$CH$_3$), 1.9–2.6 (m, 3-CH$_2$ & 4-CH$_2$), 2.40 (s, CH$_3$C(O)CH$_2$), 3.86 (s, OCH$_3$), 3.90 (s, 2 OCH$_3$), 4.12 (t, OCH$_2$CH$_2$CH$_3$), 4.42 (s, CH$_3$C(O)CH$_2$), 5.10–5.28 (m, 2-CH & 5-CH), 6.64 (s, 5-ArH), 7.35 & 7.47(2 d, 2-ArH).

STEP 1M: (−)-(2S,5S)-2-[3-(2-Oxopropylsulfonyl)-4-n-propoxy-5-hydroxyphenyl]-5-(3,4,5-trimethoxyphenyl) tetrahydrofuran This compound was prepared from (−)-trans-(2S,5S) 2-[3-(2-oxopropylsulfonyl)-4-n-propoxy-5-benzyloxyphenyl]-5-(3,4,5-trimethoxyphenyl) tetrahydrofuran as shown above in the racemic case STEP L: NMR(200 MHz, CDCl$_3$) δ 1.10 (t, CH$_2$CH$_2$CH$_3$), 1.92(m, CH$_2$CH$_2$CH$_3$), 1.9–2.6(m, 3-CH$_2$ & 4-CH$_2$), 2.40 (s, CH$_3$C(O)CH$_2$), 3.86(s, OCH$_3$), 3.90 (s, 2 OCH$_3$), 4.12(t, OCH$_2$CH$_2$CH$_3$), 4.42 (s, CH$_3$C(O)CH$_2$), 5.10–5.28(m, 2-CH & 5-CH), 6.64(s, 5-ArH), 7.35 & 7 47(2 d, 2-ArH).

STEP 1N: 2-[3-(2-Oxopropylsulfonyl)-4-n-propxy-5-[3-(N,N-dimethylamino)-n-propoxy]phenyl]-5-(3,4,5-trimethoxyphenyl)-tetrahydrofuran A mixture of 300 mg of trans 2-[3-(2-oxo-propylsulfonyl)-4-n-propoxy-5- hydroxyphenyl]5-(3,4,5-trimethoxyphenyl)tetrahydrofuran, 6 mL acetone, 150 mg 3-bromopropyl- N,N-dimethylamine hydrochloride, and 150 mg K$_2$CO$_3$ was heated at 50° for 16 hrs and filtered. Evaporation of the filtrate and purification by prep. TLC on silica plates (ethyl acetate) gave the title compound as a colorless gum: NMR (200 MHz, CDCl$_3$) δ 1.06 (t, CH$_2$CH$_2$CH$_3$), 1.88 (m, CH$_2$CH$_2$CH$_3$), 2.39 (s, CH$_3$C(O)CH$_2$), 2.30 (s, N(CH$_3$)$_2$), 2.40–2.58 (m, CH$_2$N(CH$_3$)$_2$)$_2$, 3.85 (s, OCH$_3$), 3.88 (s, 2 OCH$_3$), 4.12 & 4.15 (t, 2 ArOCH$_2$), 4.46 (s, CH$_3$C(O)CH$_2$), 5.10–5.30 (m, 2-CH & 5-CH), 6.62 (s, 5-ArH), 7.30 & 7.44 (2 d, 2-ArH).

EXAMPLE 2 trans-2-[3-(2-Oxopropylsulfonyl)-4-propoxy-5-(w-bromoalkoxy)phenyl]-5-(3,4,5-trimethoxyphenyl) tetrahydrofuran.

Dibromoalkane (100 uL) was added to a solution of trans-2-[3-(2-oxopropylsulfonyl)-4-propoxy-5-(hydroxy)phenyl]-5-(3,4,5-trimethoxyphenyl)tetrahydrofuran (100 mg) [Example 1, Step L] in acetone (100 mL) containing K$_2$CO$_3$ (100 mg), and the mixture was heated at 50° C. for 16 h and filtered. The filtrate was concentrated to a residue, which was purified by preparative TLC (hexane-ethyl acetate; 3:2, v/v) to give the desired products. By these procedures were prepared the following compounds.

EXAMPLE 2A trans-2-[3-(2-Oxopropylsulfonyl)-4-propoxy-5-(2-bromoethoxy)phenyl]-5-(3,4,5-trimethoxyphenyl) tetrahydrofuran had NMR (CDCl$_3$) δ 1.1(t, CH$_2$CH$_2$CH$_3$), 1.85 (m, CH$_2$CH$_2$CH$_3$), 2.0 & 2.49 (2 m, H-3 & H-4), 2.4 (s, CH$_2$COCH$_3$), 3.7 (t, CH$_2$CH$_2$Br), 3.81 & 3.86 (2 s, 3 OCH$_3$), 4.2 (t, CH$_2$CH$_2$Br), 4.4 (t, CH$_2$CH$_2$CH$_3$), 4.46 (s, CH$_2$COCH$_3$), 5.20 (2 m, H-2 & H-5), 6.60 (s, C$_5$ArH), 7.22 & 7.45 (2 d, J=1.5 Hz, C$_2$ArH).

EXAMPLE 2B trans-2-[3-(2-Oxopropylsulfonyl)-4-propoxy-5-(3-bromopropoxy)phenyl]-5-(3,4,5-trimethoxyphenyl) tetrahydrofuran had NMR (CDCl$_3$) δ NMR (CDCl$_3$).δ 1.1 (t, CH$_2$CH$_2$CH$_3$), 1.84(m, CH$_2$CH$_2$CH$_3$) 1.94 (m, CH$_2$CH$_2$CH$_2$), 2.0 & 2.49 (2 m, H-3 & H-4), 2.4 (s, CH$_2$COCH$_3$), 3.7 (2 t, CH$_2$Br), 3.81 & 3.86 (2 s, 3 OCH$_3$), 4.14 (t, CH$_2$CH$_2$CH$_2$Br), 4.25 (t, CH$_2$CH$_2$CH$_3$), 4.46 (s, CH$_2$CO), 5.20 (m, H-2 & H-5), 6.60 (s, C$_5$ArH), 7.36 & 7.50 (2 d, J=1.5 Hz, C$_2$ArH).

EXAMPLE 2C trans-2-[3-(2-Oxopropylsulfonyl-4-propoxy-5-(4-bromobutoxy)phenyl]-5-(3,4,5-trimethoxyphenyl) tetrahydrofuran had NMR (CDCl$_3$) δ 1.08 (t, CH$_2$CH$_2$CH$_3$), 1.84 (m, CH$_2$ CH$_2$ CH$_3$) 1.94 (m, CH$_2$CH$_2$CH$_2$), 2.0 & 2.49 (2m, H-3 & H-4), 2.05 (m, CH$_2$CH$_2$CH$_2$CH$_2$), 2.4 (s, CH$_2$COCH$_3$), 3.5 (t, CH$_2$Br), 3.81 & 3.86 (2 s, 3 OCH$_3$), 4.1 (m, CH$_2$CH$_2$CH$_2$CH$_2$Br & CH$_2$CH$_2$CH$_3$), 4.46 (s, CH$_2$CO), 5.20 (m, H-2 & H-5), 6.60 (s, C$_5$ArH), 7.24 & 7.43 (2 d, J=1.5 Hz, C$_2$ArH).

EXAMPLE 3 trans-2-[3-(2-Oxopropylsulfonyl)-4-n-propoxy-5-(3-hydroxypropoxy)phenyl]-5-(3,4,5-trimethoxyphenyl)tetrahydrofuran A mixture of trans-2-[3-(2-oxopropylsulfonyl)-4-n-propoxy-5-hydroxyphenyl]-5-(3,4,5-trimethoxyphenyl)tetrahydrofuran (30 mg, 0.059 mmol), 3-bromo-1-propanol (12 uL, 0.13 mmol) and potassium carbonate (17 mg, 0.12 mmol) in DMF (0.5 mL) was heated at 80° C. with stirring under nitrogen for 1 h. The reaction mixture was cooled and diluted with ethyl ether. It was washed with water (2×), brine, dried, filtered, and evaporated to a residue (33 mg), which was purified by preparative TLC (hexane ethyl acetate; 7:3, v/v) to give the title compound (20 mg, 61%): $R_f$ 0.3; NMR (CDCl$_3$) δ 2.38 (s, SO$_2$CH$_2$COCH$_3$), 4.15 & 4.24 (2 t, OCH$_2$CH$_2$), 4.48 (s, SO$_2$CH$_2$), 5.22 (m, H-2 & H-5).

EXAMPLE 4 trans-(2S,5S)-2-[3-(2-Oxopropylsulfonyl)-4-n-propoxy-5-(3-hydroxypropoxy)phenyl]-5-(3,4,5-trimethoxyphenyl)tetrahydrofuran.

This compound was prepared from trans-(2S,5S) 2-[3-(2-oxopropylsulfonyl)-4-n-propoxy-5-hydroxyphenyl]-5-(3,4,5-trimethoxyphenyl) tetrahydrofuran (Example 1, Step M) according to procedures outlined in Example 3.

EXAMPLE 5 trans-(2S,5S)-2-[3-(2-Oxopropylsulfonyl)-4-n-propoxy-5-(3-phospho-propoxy)phenyl]-5-(3,4,5-trimethoxyphenyl)tetrahydrofuran.

The title compound was prepared by stirring a solution of trans-(2S,5S)-2-[3-(2-oxopropylsulfonyl)-4-n-propoxy 5-(3-hydroxypropoxy)phenyl]-5-(3,4,5-trimethoxyphenyl)tetrahydrofuran, and dibenzylchlorophosphate, in THF with an equivalent of triethylamine at 0° C. The resulting dibenzyl phosphate ester was purified by chromatography on silica gel and liberated to the title compound by hydrogenation in methanol at 40 psi using 5% Pd/C as catalyst.

An alternate method of preparation is as follows:

STEP 5A: (−) trans-(2S,5S)-[3-(2-Oxppropylsulfonyl-4-n-propoxy-5-(3-dibenzyloxyphosphorylpropoxy)-phenyl]-5-(3,4,5-trimethoxyphenyl)tetrahydrofuran Dimethyl azodicarboxylate (11.4 g, 0.08 mol) was added dropwise to a stirred solution of (−) trans-(2S,5S)-[3-(2-Oxopropylsulfonyl)-4-n-propoxy 5-(3-hydroxypropoxy)phenyl]-5-(3,4,5-trimethoxyphenyl)-tetrahydrofuran (29.5 g, 0.05 mol), triphenylphosphine (20.48 g, 0.08 mol), and dibenzylphosphate (21.73 g, 0.08 mol) in THF (200 mL) at 0° C. The mixture was stirred at room temperature for 2 hours and concentrated to a residue which was purified by column chromatography on silica gel (dichloromethaneacetone, 9:1; v/v). The product was isolated as an oil (35 g, 83%) which was crystallized from cold methanol. Recrystallization from i-propanol afforded pure title compound: mp 81°–83° C.; [a]$_D$-45° (c 1.0, CHCl$_3$); NMR (CDCl$_3$) δ 1.02 (t, CH$_2$CH$_2$CH$_3$), 2.16 (s, SO$_2$CH$_2$COCH$_3$), 4.44 (bs, SO$_2$CH$_2$COCH$_3$), 5.04 (m, OCH$_2$Ar), 6.62 (s, C$_5$ArH) 7.24 & 7.47 (2 d, C$_2$ArH) and 7.32 (bs, OCH$_2$C$_6$H$_5$)

Step 5B: (−)trans-(2S,5S)-[3-(2-Oxopropylsulfonyl)-4-n-propoxy-5-{3-(phosphonooxy)propoxy}phenyl]-5-(3,4,5-trimethoxyphenyl)tetrahydrofuran monopotassium salt A solution of (−)trans-(2S,5S)-[3-(2-Oxopropylsulfonyl)-4-n-propoxy-5-(3-dibenzyloxyphosphorylpropoxy)phenyl]-5-(3,4 5-trimethoxyphenyl)tetrahydrofuran (5 g, 6.05 mmol) in ethyl acetate (80 mL) and triethylamine (1.85 mL, 13.4 mmol) was hydrogenated over 10% palladium on charcoal (1.0 g) at 40 psi for 1 hour. The catalyst was filtered off through Celite and the filtrate was concentrated to dryness. The resulting oil was taken up in methanol water (1:1, v/v) and the solution was put on a column of AG 50W resin (K+; 200 mL) and eluted with the same solvent system. Fractions containing the desired compound were combined, evaporated to a small volume, and lyophilized to give the title compound. (3.3 g, 80%):[a ]$_D$-53° (c 1.0, MeOH); NMR (CDCl$_3$) δ 0.98 (t, CH$_2$CH$_2$CH$_3$), 2.31 (s, SO$_2$CH$_2$COCH$_3$), 4.42 (s, SO$_2$CH$_2$COCH$_3$), 5.16 (m, H-2 & H-5), 6.6 (s, C$_5$ArH), 7.28 and 7.44 (d, C$_2$ArH).

Anal. for C$_{28}$H$_{38}$KO$_{13}$PS.H$_2$O: Cal'd: C, 47.86; H, 5.74; K, 5.56. Found: C, 47.85; H, 5.76; K, 5.34.

Alternate Preparation of (−)trans-(2S,5S)-[3-(2-Oxopropylsulfonyl)-4-n-propoxy-5-{3-(phosphonooxy)propoxy}phenyl]5-(3,4,5-trimethoxyphenyl)tetrahydrofuran monopotassium salt.

trans-(2S,5S) [3-(2-Oxopropylsulfonyl)-4-propoxy-5-(3-dibenzylphosphopropoxy)phenyl]-5-(3,4,5-trimethoxyphenyl) tetrahydrofuran (10.75 g, 1.3 mmoles) was dissolved in methanol (200 mL) and KHCO$_3$ (1.3 g, 1.3 mmoles in 4 ml) was added. The mixture was hydrogenated using 10% Pd/C (1.2 g.) at 40 psi for 1 hour and then filtered through celite washed with water and concentrated to a small volume of water and lyophilized yielding the mono potassium salt (8.7 g) 98%. This material could be further purified by reverse phase HPLC if required. NMR(200 MHz, CDCl$_3$) δ 0.98(t, CH$_2$CH$_2$CH$_3$), 2.31 (s, SO$_2$CH$_2$COCH$_3$), 4.42 (s, SO$_2$CH$_2$COCH$_3$), 5.16 (m, H-2 and H-5), 6.6 (s, C$_2$ArH), 7.28 and 7.44 (d, C$_5$ArH)

Anal. for C$_{28}$H$_{38}$O$_{13}$KPS.H$_2$O: Calc.: C, 47.86; H, 5.74., K, 5.56. Found: C, 47.85; H, 5.76; K, 5.34.

Alternate Preparation of trans-(2S,5S) [3-(2-Oxopropylsulfonyl)-4-propoxy 5-(3-dibenzylphosphopropoxy)phenyl]phenyl]-5-(3,4,5-trimethoxyphenyl)tetrahydrofuran Step 5C: 3-bromopropyldibenzylphosphate Dimethyl azodicarboxylate (4.38 g, 0.03 moles) was added dropwise to a stirred solution 3-bromo-1-propanol (2.78 g, 0.02 moles); triphenylphosphine (7.87 g, 0.03 moles) and dibenzylphosphate (8.35 g, 0.03 moles) in THF (80 mL) at 0° C. After 2 hours the reaction mixture was concentrated to dryness and chromatographed on silica gel and eluted with hexane/ethyl acetate (3:2) to afford 6.53 g (82%) of a colorless oil. NMR (200 MHz, CDCl$_3$) δ 2.12 (m, OCH$_2$CH$_2$CH$_2$Br), 3.42 (t, OCH$_2$CH$_2$CH$_2$Br), 4.13 (broad q, OCH$_2$CH$_2$CH$_2$Br), 5.08 (m, OCH$_2$Ar), 7.38 (s, OCH$_2$C$_6$H$_5$)

STEP 5D: (−) trans-(2S,5S)-2-dibenzylphosphopropoxy)phenyl]-5-(3,4,5-trimethoxyphenyl)tetrahydrofuran A mixture of (−)-trans-(2S,5S)-2-[3-(2-Oxopropylsulfonyl-4-n-propoxy-5-hydroxyphenyl]-5-(3,4,5-trimethoxyphenyl)tetrahydrofuran (102 mg, 0.2 mmole), 3-bromopropyldibenzylphosphate (120 mg, 0.3 mmole) and K$_2$CO$_3$ (42 mg, 0.3 mmole) in acetone (3 ml) was heated under nitrogen at 55° C. for 48 hours. The reaction mixture was cooled, filtered through celite and the filtrate was concentrated and purified by prepTLC using hexane/ethyl acetate (3:7) to afford 140 mg (85%) of the product identical to the material obtained via STEP 5A.

EXAMPLE 6 trans-2-[3-(2-Oxopropyl-sulfonyl)-4-n-propoxy-5-(2-oxopropoxy)phenyl]-5-(3,4,5-trimethoxyphenyl)tetrahydrofuran A mixture of trans-2-[3-(2- oxopropylsulfonyl)-4-n-propoxy-5-hydroxyphenyl]5- (3,4,5-trimethoxyphenyl)-tetrahydrofuran (51 mg, 0.1 mmol), chloroacetone(16 uL, 0.2 mmol) and potassium carbonate (28 mg, 0.2 mmol) in DMF (1 mL) was stirred at room temperature for 40 h. The reaction mixture was diluted with ethyl ether and washed with water and brine. The organic extracts were dried (MgSO4), filtered, and evaporated to a residue (58 mg), which was purified by preparative TLC (hexane ethyl acetate; 3:2. v/v). The title compound was isolated as a colorless foam: $R_f$ 0.38; MS, m/z 564M+.; NMR (CDCl$_3$) δ 1.08(t, CH$_2$CH$_2$CH$_3$), 2.33 & 2.38 (2 s, OCH$_2$COCH$_3$ & SO$_2$CH$_2$COCH$_3$), 4.48 (s, SO$_2$CH$_2$), 4.68 (s, OCH$_2$CO), 5.20 (m, H-2 & H-5), 6.62 (s, 2 H, C$_5$ArH), 7.20 & 7.52 (2 d, 2 H, C$_2$ArH)

EXAMPLE 7 trans-2-[3-(2-Hydroxypropylsulfonyl)-4-n-propoxy-5-benzyloxyphenyl]-5-(3,4,5-trimethoxyphenyl)tetrahydrofuran Acetaldehyde (0.7 mL, 12.4 mmol) was added under nitrogen to a solution of trans-2-[3-(2-methylsulfonyl)-4-n-propoxy-5-benzyloxyphenyl]-5-(3,4,5-trimethoxyphenyl)tetrahydrofuran (1.15 g, 2.07 mmol) and LDA (2.5 mL, 2.5 mmol; 1.5M in cyclohexane) in THF (15 mL) at −70° C. The mixture was stirred at this temperature for 10 min, and then allowed to warm to room temperature. Dichloromethane was added and the solution was washed with aq. NH$_4$C$_1$, dried, and evaporated to dryness. The residue was purified by flash column chromatography (hexane-ethyl acetate; 2:1, v/v) to give the title compound as a crystalline mass : mp 103°–110° C.; R$_f$0.17 (s. m. had R$_f$0.27; hexane-ethyl acetate; 3:2, v/v); NMR (CDCl$_3$) δ 0.98 (t, J=7.5 Hz, CH$_2$CH$_2$CH$_3$), 1.25 (d, J=6.5 Hz, CH$_2$CHOHCH$_3$), 3.86 (s, OCH$_3$), 3.89 (s, 2 OCH$_3$), 5.18 (s, CH$_2$Ph), 6.63 (s, 2 H, C$_5$ArH).

EXAMPLE 8 trans-2-[3-(2-Hydroxypropylsulfonyl)-4-propoxy 5-hydroxyphenyl]-5-(3,4,5-trimethoxyphenyl) tetrahydrofuran A solution of trans-2-[3-(2hydroxypropylsulfonyl)-4-propoxy-5-benzloxyphenyl]-5-(3,4,5-trimethoxyphenyl)tetrahydrofuran (1.07 g, 1.78 mmol) in ethyl acetate (5 mL) was hydrogenated over 10% palladium-over charcoal (200 mg) for 1 h. The catalyst was filtered off and washed with ethyl acetate. The filtrates were combined and evaporated to a syrup R$_f$0 (hexane-ethyl acetate; 1:1, v/v); NMR (CDCl$_3$) δ 1.08 (t, J=7.5 Hz, CH$_2$CH$_2$CH$_3$), 1.25 (d, J=6.5 Hz, CH$_2$CHOHCH$_3$), 3.86 (s, OCH$_3$), 3.88 (s, 2 OCH$_3$), 5.15–5.26 (m, H-2 & H-5), 6.62 (s, 2 H, C$_5$ArH), 7.34 & 7.50 (2 d,d, 2 H, C$_2$ArH).

EXAMPLE 9A trans-2-[3-(2-hydroxypropylsulfonyl)-4-n-propoxy-5-(3-hydroxypropoxy)phenyl]-5-(3,4,5-trimethoxyphenyl)-tetrahydrofuran This compound was prepared from trans-2-[3-(2-Hydroxypropylsulfonyl)-4-n-propoxy-5-hydroxyphenyl]-5-(3,4,5-trimethoxyphenyl)tetrahydrofuran according to procedures outlined in Example 3. This compound had NMR (CDCl$_3$) δ 1.06 (t, CH$_3$CH$_2$CH$_2$), 1.26 (d, CH$_3$CHOH), 1.92 (m, CH$_3$CH$_2$CH$_2$O, 1.9–2.65 (m, 3 & 4 -CH$_2$), 2.14 (t, OCH$_2$CH$_2$CH$_2$O), 3.3–3.6 (m, SO$_2$CH$_2$). 3.84 (s, OCH$_3$), 3.87 (s, 2 OCH$_3$), 4.1–4.3 (m, OCH$_2$Ar), 5.11–5.3 (m, 2+5-CH), 6.62 (s, 5-ArH), 7.3+7.5 (dd, 2Ar-H).

EXAMPLE 9B (−) trans-(2S,5S)-2 [3-{(2S)-2-Hydroxypropylsulfonyl}-4-n-propoxy-5-(3-hydroxypropoxy)phenyl]-5-(3,4,5-trimethoxyphenyl)-tetrahydrofuran and (−)-trans-(2S,5S)-2-[3-{(2R)-2-Hydroxypropylsulfonyl}-4-n-propoxy-5-(3-hydroxypropoxy)phenyl]-5-(3,4,5-trimethoxyphenyl)tetrahydrofuran (9B-S) and (9B-R)

STEP 1: (−)-trans-(2S,5S)-2-[3-(2-Hydroxypropylsulfonyl)-4-n-propoxy-5-benzyloxyphenyl]-5-(3,4,5-trimethoxyphenyl)tetrahydrofuran Acetaldeyde (1.85 mL, 33.2 mmol) was added under nitrogen to a solution of (−)-trans-(2S,5S)-2-(3-Methylsulfonyl-4-n-propoxy-5-benzyloxyphenyl)-5-(3, 4,5-trimethoxyphenyl)tetrahydrofuran (3.0 g, 5.4 mmol) and LDA (6.5 mL, 9.8 mmol; 1.5M in cyclohexane) in THF (30 mL) at −70° C. The reaction mixture was stirred at this temperature for 10 minutes and allowed to warm to room temperature. Dichloromethane was added and the solution was washed with aqueous NH$_4$Cl, dried, and evaporated to dryness. The residue was put on a flash column of silica gel and eluted with hexane-ethyl acetate (2:1 followed by 3:2, v/v). The title compound was isolated as a crystalline mass. Recrystallization from CH$_2$Cl$_2$-Et$_2$O afforded pure title compound. (2.43 g, 75%): R$_f$0.26 (hexane-ethyl acetate, 3:2; v/v); mP Anal. for C$_{32}$H$_{40}$O$_9$S: Calc.: C, 63.98., H, 6.71., S, 5.34. Found: C, 63.83; H, 6.68., S, 5.19.

Step 2: Mandelate Esters of (−)-trans-(2S,5S)-2-[3-(2-Hydroxypropylsulfonyl)-4-n-propoxy-5-benzyloxy-phenyl)-5-(3,4,5-trimethoxyphenyl)tetrahydrofuran.

1,3-Dicyclohexylcarbodiimide (2.35 g, 11.4 mmol) was added to a solution of (−)-trans-(2S,5S)-2-[3-(2-Hydroxypropylsulfonyl)-4-n-propoxy-5-benzyloxy-phenyl)-5-(3,4,5-trimethoxyphenyl)tetrahydrofuran (2.35 g, 3.9 mmol), (−)-R-O-methylmandelic acid (1.9 g, 11.4 mmol), and 4 dimethylaminopyridine (0.16 g, 1.3 mmol) in dry dichloromethane (40 mL) and the mixture was stirred under nitrogen at room temperature for 3 hours. The urea was filtered off and the filtrate was evaporated to a residue which was purified by flash column chromatography (hexane ethyl acetate, 3:1; v/v) to give a 1:1 mixture of the diastereomeric mandelate esters (2.7 g). The mixture was repurified by flash column chromatography with CH$_2$-Cl$_2$ hexane-EtOAc (50:35:15, v/v) as the eluant and the two mandelate esters were separated by MPLC using the same solvent system. The absolute stereochemistry of the two compounds was assigned by NMR using the Mosher model depicted in the extended Newman projection. The respective S,S,R and S,S,S compounds are designated 9B-R and 9B-R. 9B-R had NMR (CDCl$_3$) δ 0.94 (t, J=7.5 Hz, CH$_2$CH$_2$CH$_3$), 1.37 (d, J=6.5 Hz, CHCHOMCH$_3$), 1.77 (m, CH$_2$CH$_2$CH$_3$), 3.39 (s, COCH(OCH$_3$)Ph), 3.51 (2 d, J=6.0 & 13.5 Hz, SO$_2$CH$_A$H$_B$), 3.71 (2 d, J=5.5 & 13.5 Hz, SO$_2$CH$_A$H$_B$), 3.86 (s, OCH$_3$), 3.88 (s, 2 OCH$_3$), 4,12 (t, J=6.5 Hz, CH$_2$CH$_2$CH$_3$), 4.67 (s, COCH(OCH$_3$)Ph), 5.15 (s, OCH$_2$Ph), 6.61 (s, C$_5$ArH). Compound 9B-S (bottom spot) had NMR (CDCl$_3$)δ0.98 (t,J=7.0 Hz, CH$_2$CH$_2$CH$_3$),1.14 (d, J=6.0 Hz, CHCHOMCH$_3$), 1.82 (m, CH$_2$CH$_2$CH$_3$), 3.36 (s, COCH(OCH$_3$)Ph), 3.54 (2 d, J=4.0 & 14.5 Hz, SO$_2$CH$_A$H$_B$), 3.79 (2 d, J=7.5 & 14.5 Hz, SO$_2$CH$_A$H$_B$), 3.86 (s, OCH$_3$), 3.88 (s, 2OCH$_3$), 4, 17 (t, J=6.5 Hz, CH$_2$CH$_2$CH$_3$), 4.49 (s, COCH(OCH$_3$)Ph), 5.18 (s, OCH$_2$Ph), 6.62 (s, C$_5$ArH).

Step 3: (−)-trans-(2S,5S)-2-[3-{(2S)-2-Hydroxypropylsulfonyl}-4-n-propoxy-5-benzyloxyphenyl)-5-(3,4,5-trimethoxyphenyl)tetrahydrofuran Lithium aluminum hydride (0.49 mL, 0.49 mmol; 1.0M solution in THF) was added under nitrogen to a solution of compound 9B-S (727 mg, 0.97 mmol) in dry THF (25 mL) at 0°–5° C. After 2 h at room temperature, the solution was cooled and glacial acetic acid (15 drops) was added until it became neutral. Dichloromethane was added and the solution was washed with cold 2N HCl, brine, dried, and evaporated to dryness. The mixture was separated by flash column chromatography (hexane ethyl acetate, 2:1; v/v) to give some unreacted starting material (37 mg) and the title compound as a crystalline mass. Slow recrystallization of the product from methanol afforded pure material (470 mg, 85% based on the used s.m.): mp 117°–118° C.; [a]$_D$ −42.2° (c 1.2, CHCl$_3$); NMR (CDCl$_3$) δ 0.98 (t, J=7.0 Hz, CH$_2$CH$_2$CH$_3$), 1.25 (d, J=6.0 Hz, CHCHOHCH$_3$), 1.83 (m, CH$_2$CH$_2$CH$_3$), 1.89–2.09 & 2.38–2.57 (2 m, H-3 & H-4), 3.41 (2 d, J=9.0 & 14.0 Hz, SO$_2$CH$_A$H$_B$), 3.62 (2 d, J=1.5 & 14.0 Hz, SO$_2$CH$_A$H$_B$), 3.86 (s, OCH$_3$), 3.90 (s, 2OCH$_3$), 5.18 (s, OCH$_2$Ph), 5.10–5.30 (m, H-2 & H-5), 6.62 (s, C$_5$ArH), 7.34–7.46 (ArH).

STEP 4: (−)-trans-(2S,5S)-2-[3-{(2R)-2-Hydroxypropylsulfonyl}-4-n-propoxy-5-benzyloxyphenyl)-5-(3,4,5-trimethoxyphenyl)tetrahydrofuran This compound was prepared from 9B-R similarly as described for 9B-S. It had mp 123°–125° C. (CH$_2$Cl$_2$-Et$_2$O); [a]$_D$ −68.8° (c 1.1, CHCl$_3$); NMR(CDCl$_3$) δ0.98 (t, J=7.5 Hz, CH$_2$CH$_2$CH$_3$), 1.24 (d, J=6.5 Hz, CHCHOHCH$_3$), 1.82 (m, CH$_2$CH$_2$CH$_3$), 3.40 (2 d, J=9.0 & 14.0 Hz, SO$_2$CH$_A$H$_B$), 3.60 (2 d, J=1.5 & 14.0 Hz, SO$_2$CH$_A$H$_B$), 3.86 (s, OCH$_3$), 3.89 (s, 2 OCH$_3$), 5.17 (s OCH$_2$Ph), 6.62 (s, C$_5$ArH).

STEP 5: (−)-trans-(2S,5S)-2-[3-{(2S)-2-Hydroxypropylsulfonyl}-4-n-propoxy-5-hydroxyphenyl)-5-(3,4,5-trimethoxyphenyl)tetrahydrofuran A solution of (−)-trans-(2S,5S)-2-[3-{(2S)-2-Hydroxypropylsulfonyl}-4-n-propoxy-5-benzyloxyphenyl)-5-(3,4,5-trimethoxyphenyl)tetrahydrofuran (470 mg, 0.78 mmol) in ethyl acetate (5 mL) was hydrogenated over 10% palladium on-charcoal (94 mg) for 1 h. The catalyst was filtered off and washed with ethyl acetate. The filtrates were combined and evaporated to a syrup (371 mg, 93%) which was used directly in the next experiment without further purification. The title compound had R$_f$ 0.09 (hexane-ethyl acetate, 3:2; v/v); NMR (CDCl$_3$) δ 1.09 (t, J=7.5 Hz, CH$_2$CH$_2$CH$_3$), 1.25 (d, J=6.5 Hz, CHCHOHCH$_3$), 3.86 (s, OCH$_3$), 3.89 (s, 2 OCH$_3$), 5.13–5.28 (m, H-2 & H-5), 5.75 (s, OH), 6.62 (s, C$_5$ArH), 7.34 & 7.48 (2 d, J=2.0 Hz each, C$_2$ArH).

STEP 6:
(−)-trans-(2S,5S)-2-[3-{(2S)-2-Hydroxypropylsulfonyl}-4-n-propoxy-5-(3-hydroxypropoxy)phenyl]-5-(3,4,5-trimethoxyphenyl)tetrahydrofuran A mixture of (−)-trans-(2S,5S)-2-[3-{(2S)-2-Hydroxypropylsulfonyl}-4-n-propoxy-5-hydroxyphenyl)-5-(3,4,5-trimethoxyphenyl)tetrahydrofuran (371 mg, 0.73 mmol), 3-bromo-1-propanol (0.12 mL, 1.31 mmol), and potassium carbonate (181 mg, 1.31 mmol) in DMF (3 mL) was heated under nitrogen at 75° C. (bath temperature) for 1.5 h. The reaction mixture was cooled and partitioned between ethyl ether and water. The aqueous layer was re-extracted with Et$_2$O (2x). The ethereal layer was dried (MgSO$_4$) and evaporated to dryness. The crude product was purified by flash column chromatography (hexane-ethyl acetate, 1:1 to 1:2, v/v) to give the title compound as a syrup (351 mg, 85%): [a]$_D$ −46.8° (c 1.7, CHCl$_3$); MS m/z 568 (M+°); NMR (CDCl$_3$) δ 1.04 (t, J=7.5 Hz, CH$_2$CH$_2$CH$_3$), 1.24 (d, J=6.5 Hz, CHCHOHCH$_3$), 3.40 (2 d, J=9.0 & 14.0 Hz, SO$_2$CH$_A$H$_B$), 3.58 (2 d, J=2.0 & 14.0 Hz, SO$_2$CH$_A$H$_B$), 3.85 (s, OCH$_3$), 3.88 (s, 2 OCH$_3$), 4.11 (m, CH$_2$CH$_2$CH$_3$), 4.22 (m, CH$_2$CH$_2$CH$_2$OH), 5.14–5.29 (m, H-2 & H-5), 6.62 (s, C$_5$ArH), 7.32 & 7.48 (2 d, J=2.0 each, C$_2$ArH).

STEP 7: (−)-trans-(2S,5S)-2-[3-{(2R)-2-Hydroxypropylsulfonyl}-4-n-propoxy-5-(3-hydroxypropoxy)phenyl]-5-(3,4,5-trimethoxyphenyl)tetrahydrofuran This compound was prepared from (−)-trans-(2S,5S)-2-[3-{(2R)-2-Hydroxypropylsulfonyl}-4-n-propoxy-5-benzyloxyphenyl)-5-(3,4,5-trimethoxyphenyl)tetrahydrofuran similarly as described for the preparation of (−)-trans-(2S,5S)-2-[3-{(2S)-2-Hydroxypropylsulfonyl}-4-n-propoxy-5-(3-hydroxypropoxy)phenyl]-5-(3,4,5-trimethoxyphenyl)tetrahydrofuran. It had [a]$_D$−66.2° (c 1.8, CHCl$_3$); MS m/z 568 (M+.); NMR (CDCl$_3$ δ 1.04 (t, J=7.5 Hz, CH$_2$CH$_2$CH$_3$), 1.25 (d, J=6.5 Hz, CHCHOHCH$_3$), 3.41 (2 d, J=9.0 & 14.0 Hz, SO$_2$CH$_A$H$_B$), 3.58 (2 d, J=2.0 & 14.0 Hz, SO$_2$CH$_A$H$_B$), 3.85 (s, OCH$_3$), 3.88 (s, 2 OCH$_3$), 4.11 (m, CH$_2$CH$_2$CH$_3$), 4.22 (m, CH$_2$CH$_2$CH$_2$OH), 5.14–5.29 (m, H-2 & H-5), 6.62 (s, C$_5$ArH), 7.29 & 7.50 (2 d, J=2.0 each, C$_2$ArH).

EXAMPLE 9C (−)trans-(2S,5S)-2-[3-{(2S)-2-Hydroxypropylsulfonyl}-4-n-propoxy-5-{3-(phosphonooxy)propoxy}phenyl]-5-(3,4,5-trimethoxyphenyl)tetrahydrofuran monopotassium salt Step 1: (−)-trans-(2S,5S)-2-[3-{(2S)-2-Hydroxypropylsulfonyl}-4-n-propoxy-5-(3-dibenzyloxyphosphorylpropoxy)phenyl]-5-(3,4,5-trimethoxyphenyl)tetrahydrofuran Dimethyl azodicarboxylate (0.034 mL, 0.24 mmol) was added under nitrogen to a stirred solution of (−)-trans-(2S,5S)-2-[3-{(2S)-2-Hydroxypropylsulfonyl}-4-n-propoxy5-(3-hydroxypropoxy)phenyl]-5-(3,4,5-trimethoxyphenyl)tetrahydrofuran (89 mg, 0.16 mmol), triphenylphosphine (61.5 mg, 0.24 mmol), and dibenzylphosphate (65.3 mg. 0.24 mmol) in dry THF (3 mL) at 0° C. After 1.5 hours at room temperature, the reaction mixture was concentrated to dryness and the residue was purified by preparative TLC (hexaneethyl acetate, 3:1; v/v) to give the desired product zone (116 mg)

which was extracted with ethyl acetate. This material was then repurified by preparative TLC (dichloromethane acetone, 9:1; v/v) to give the title compound (62 mg, 48%): $R_f$ 0.46 ($CH_2Cl_2$-acetone, 9:1; v/v); $[a]_D$ −30° (c 1.76, $CHCl_3$); MS m/z 828 (M+.); NMR ($CDCl_3$) δ 1.01 (t, J=7.0 Hz, $CH_2CH_2CH_3$), 1.24 (d, J=6.0 Hz, $CHCHOHCH_3$), 1.81 (m, $CH_2CH_2CH_3$). 3.39 (2 d. J=9.0 & 14.0 Hz, $SO_2CH_AH_B$), 3.57 (2 d, J=2.0 & 14.0 Hz, $SO_2CH_AH_B$), 3.86 (s, $OCH_3$), 3.88 (s, 2 $OCH_3$), 5.0 & 5.04 (2 s, $OCH_2Ph$). 5.15–5.30 (m, H-2 & H-5), 6.62 (s. $C_5ArH$). 7.26 & 7.49 (2 d, J=2.0 each, $C_2ArH$). 7.31 (s, $OCH_2C_6H_5$).

Anal. for $C_{42}H_{53}O_{13}PS.1.93 H_2O$: Calc.: C, 58.41; H, 6.61. Found: C, 58.40; H, 6.52.

Step 2: (−)trans-(2S,5S)-2-[3-{(2S)-2-Hydroxypropylsulfonyl}-4-n-propoxy-5-{3-(phosphonooxy)-propoxy}phenyl]-5-(3,4,5-trimethoxyphenyl)tetrahydrofuran monopotassium salt.

A solution of (−)-trans-(2S,5S)-2-[3-{(2S)-2-Hydroxypropylsulfonyl}-4-n-propoxy-5-(3-dibenzyloxyphosphorylpropoxy)phenyl]-5-(3,4,5-trimethoxyphenyl)tetrahydrofuran (53 mg) in methanol (3 mL) containing potassium bicarbonate (6.9 mg) was hydrogenated at 45 psi over 10% Palladium-on-charcoal (11.5 mg) for 2 hours. The catalyst was filtered off and washed with methanol. The filtrates were combined and evaporated to a residue which was dissolved in water and lyophilized (44 mg, 100%). An analytical sample was purified by MPLC with a reversed phase $C_{18}$ column (water acetonitrile, 75:21; v/v). The material was regenerated monopotassium salt by passing through a column of AG 50W resin ($K^+$; 5 mL) with methanol-water (1:1, v/v) as the eluant. Fractions containing the desired compound were combined, concentrated, redissolved in water, and lyophilized to give a white fluffy material: $[a]_D$ −41.2° (c 1.02, water); NMR ($CDCl_3$) δ 1.08 (t, J=7.5 Hz, $CH_2CH_2CH_3$), 1.24 (d, J=6.5 Hz, $CHCHOHCH_3$). 1.87 (m, $CH_2CH_2CH_3$), 2.17 (m, $CH_2CH_2CH_2OP$). 1.90–2.08 & 2.40–2.64 (2m, H-3 & H-4), 3.49 (2 d, J=5.0 & 13.0 Hz, $SO_2CH_AH_B$). 3.64 (2 d, J=6.5 & 13.0 Hz, $SO_2CH_AH_B$), 3.77 (s, $OCH_3$), 3.86 (s, 2 $OCH_3$), 4.05, 4.15 & 4.28 (3 m, 3 $OCH_2$), 5.20–5.15 (m, H-2 & H-5), 6.74 (s, $C_5ArH$), 7.43 & 7.49 (2 d, J=1.0 each, $C_2ArH$).

EXAMPLE 9D (−)trans-(2S,5S)-2-[3-{(2R)-2-Hydroxypropylsulfonyl}-4-n-propoxy-5-{3-(phosphonooxy)propoxy}phenyl]-5-(3,4,5-trimethoxyphenyl)tetrahydrofuran monopotassium salt This compound was prepared in the same manner as described in Example 9C.

EXAMPLE 10 trans-2-[3-(2-hydroxypropylsulfonyl)-4-n-propoxy-5-(2-oxopropoxy)phenyl]-5-(3,4,5-trimethoxy-phenyl)tetrahydrofuran.

This compound was prepared according to the procedures outlined in example 3 except using chloroacetone in place of 3-bromo-1-proponol. This compound had NMR ($CDCl_3$) δ 1.06 (t, $CH_3CH_2CH_2$), 1.25 (d, $CH_3CHOH$), 1.90 (m, $CH_3CH_2CH_2O$), 1.8–2.6 (m, 3 4-$CH_2$), 2.34 (s, $CH_3CO$), 3.3–3.7 (m, $SO_2CH_3$), 3.85 (s, $OCH_3$), 3.88 (s, 2$OCH_3$), 4.1–4.3 (m, 2 $OCH_2Ar'$), 5.1–5.3 (m, 2+5-CH), 6.62 (s, 5-Ar-H), 7.16 as 7.56 (dd, 2-Ar-H).

EXAMPLE 11 trans-2-[3-(2-Aminopropylsulfonyl)-4-n-propoxy-5-(3-hydroxypropoxy)phenyl]5-(3,4,5-trimethoxyphenyl)tetrahydrofuran.

Sodium acetate (21 mg, 0.25 mmol) and hydroxylamine hydrochloride (21 mg, 0.2 mmol) were added to a solution of trans-2-[3-(2-oxopropylsulfonyl)-4-n-propoxy-5-(3-hydroxypropoxy)phenyl]-5-(3,4,5-trimethoxyphenyl)tetrahydrofuran (56 mg, 0.1 mmol) in ethanol (1.5 mL). The mixture was stirred at room temperature for 18 h and evaporated to dryness. The residue was partitioned between dichloromethane and water. The organic layer was washed with water and brine, dried, and evaporated to give the oxime intermediate (60 mg, 100%): $R_f$ 0.4 (hexane-ethyl acetate; 3:7, v/v); NMR ($CDCl_3$) δ 1.96 & 2.06 [C(=$NOCH_3$)$CH_3$], 3.68 & 3.82 [C(=$NOCH_3$)$CH_3$]. $BH_3$.THF (1 M in THF; 0.6 mL, 0.06 mmol) was added dropwise to a stirred solution of the above oxime (40 mg, 0.67 mmol) in THF (0.4 mL). The reaction mixture was heated at 50° C. under nitrogen for 6 h and stirred at room temperature overnight. The mixture was treated with water (0.02 mL) and 5 N NaOH (0.02 mL). After 2 h at room temperature, the mixture was diluted with dichloromethane and washed with water (2 x) and brine, dried, and evporated to a residue (37 mg). Purification by preparative TLC ($CH_2Cl_2$-MeOH; 95:5, v/v) gave the title compound as a colorless foam: $R_f$ 0.15; MS, m/z 567 M+.; NMR ($CDCl_3$) δ 1.19 [d, $CH(NH_2)CH_3$].

EXAMPLE 12 trans-2-[3-(2-N-Methylaminopropylsulfonyl)-4-n-propoxy-5-(3-hydroxypropoxy)phenyl]-5-(3,4,5-trimethoxyphenyl)tetrahydrofuran.

A mixture of trans-2-[3-(2-oxopropylsulfonyl)-4-n-propoxy-5-(3-hydroxypropoxy)phenyl]-5-(3,4,5-trimethoxyphenyl)tetrahydrofuran (56 mg, 0.1 mmol) and aq. methylamine (40%; 17 μL, 0.2 mmol) in ethanol (0.5 mL) was stirred at room temperature for 1 h. Sodium borohydride (23 mg, 6 mmol) was added and the mixture was stirred for another 1.5 h, and partitioned between dichloromethane and water. The organic layer was washed with water and brine, dried, and evaporated to a residue (56 mg). Purification by preparative TLC ($CH_2Cl_2$-MeOH; 9:1, v/v) gave the title compound as a colorless foam $R_f$ 0.5; MS, m/z 581 M+.; NMR ($CDCl_3$) δ 1.20 [d, $CH(NHCH_3)CH_3$], 2.40 [s, $CH(NHCH_3)CH_3$].

Following the procedures outlined in Example 11 was prepared the following compounds.

EXAMPLE 13 trans-2-[3-(2-N,N-dimethylaminopropyl-sulfonyl)-4-n-propoxy-5-(3-hydroxypropoxy)phenyl]5-(3,4,5-trimethoxyphenyl)tetrahydrofuran.

This compound had characteristic NMR ($CDCl_3$) δ 1.22 [bd, $CH(NMe_2)CH_3$], 2.18 [s, N($CH_3$)$_2$]

EXAMPLE 14 trans-2-[3-(2-N-Ethylaminopropylsulfonyl)-4-propoxy-5-(3-hydroxypropoxy)phenyl]-5-(3,4,5-trimethoxyphenyl)tetrahydrofuran.

This compound had characteristic NMR ($CDCl_3$) δ 1.05 & 1.08 (2 t, $CH_2CH_2CH_3$ & $NHCH_2CH_3$), 1.21 [bd, $CH(NHEt)CH_3$].

EXAMPLE 15A trans-2-[3-(2-Hydroxypropylsulfonyl)-4-propoxy-5-(2-bromoethoxy)phenyl]-5-(3,4,5-trimethoxyphenyl)tetrahydrofuran.

1,2-Dibromoethane (1.12 mL, 13 mmol) was added to a solution of trans-2-[3-(2-hydroxypropylsulfonyl)-4-propoxy-5-hydroxyphenyl]-5-(3,4,5-trimethoxyphenyl)tetrahydrofuran (331 mg, 0.65 mmol) in DMF (5 mL) containing potassium carbonate (550 mg, 3.9 mmol). The reaction mixture was heated with stirring at 70° C. for 7 h and, cooled, and partitioned between ethyl ether and water. The ethereal layer was separated and the aqueous layer was re-extracted twice with ether. The organic extracts were combined, dried, and evaporated to dryness. The product was purified by flash column chromatography on silica gel using hexane-ethyl acetate (2:1, v/v) as the eluant $R_f$ 0.42 (hexane-ethyl acetate; 1:2, v/v); NMR (CDCl$_3$) δ 1.06 (t, CH$_2$CH$_2$$\underline{CH_3}$), 1.25 (d, CH$_2$CHOH$\underline{CH_3}$), 1.90 (m, CH$_2$$\underline{CH_2}$CH$_3$), 3.74 (t, CH$_2$$\underline{CH_2}$Br), 3.83 (s. OCH$_3$), 3.88 (s. 2OCH$_3$). 5.16–5.28 (m, H-2 & H-5), 6.62 (s. 2H, C$_5$ArH), 7.28 and 7.54 (2d, 2H, C$_2$ArH).

EXAMPLE 15B trans-2-[3-(2-Hydroxypropylsulfonyl)-4-n-propoxy-5-(3-bromopropoxy)phenyl]-5-(3,4,5-trimethoxyphenyl)-tetrahydrofuran.

1,3-Dibromopropane (0.105 mL, 1.0 mol) was added to a solution of trans-2-[3-(2-hydroxypropylsulfonyl)-4-n-propoxy-5-hydroxyphenyl]-5-(3,4,5-trimethoxyphenyl)tetrahydrofuran (102 mg, 0.20 mmol) in DMF (1 mL) containing potassium carbonate (105 mg, 0.76 mmol). The reaction mixture was heated with stirring under nitrogen at 70° C. for 2 h, cooled, and partitioned between ethyl ether and water. The ethereal layer was separated and the aqueous layer was re-extracted twice with ether. The organic extracts were combined, dried, and evaporated to a residue (143 mg). Purification by preparative TLC (hexane-ethyl acetate; 1:1, v/v) gave the title compound (89 mg, 70%) as a colorless foam: $R_f$ 0.5; NMR (CDCl$_3$) δ 1.26 (d, CH$_2$CHOH$\underline{CH_3}$), 3.66 (t, CH$_2$Br).

EXAMPLE 15C trans-2-[3-(2-Hydroxypropylsulfonyl)-4-n-propoxy-5-(4-bromobutoxy)phenyl]-5-(3,4,5-trimethoxyphenyl)tetrahydrofuran.

1,4-Dibromobutane (75 μL, 0.63 mmol) was added to a solution of trans-2-[3-(2-hydroxypropylsulfonyl)-4-n-propoxy-5-hydroxyphenyl]-5-(3,4,5-trimethoxyphenyl)tetrahydrofuran (75 mg, 0.15 mmol) in DMF (0.5 mL) containing potassium carbonate (75 mg, 0.54 mmol). The reaction mixture was heated with stirring under nitrogen at 70° C. for 1.5 h, cooled, and partitioned between ethyl ether and water. The ethereal layer was separated and the aqueous layer was re-extracted twice with ether. The organic extracts were combined, dried, and evaporated to a residue (170 mg). Purification by preparative TLC (hexane-ethyl acetate; 1:1, v/v) gave the title compound as a colorless viscous oil: $R_f$ 0.5; NMR (CDCl$_3$) δ 1.25 (d, CH$_2$CHOH$\underline{CH_3}$).

EXAMPLE 16 trans-2-[3-(2-N-Methylaminoethylsulfonyl)-4,5-di-n-propoxyphenyl]-5-(3,4,5-trimethoxyphenyl) tetrahydrofuran.

STEP 16A: 1-[3-(2-Hydroxyethylthio)-4-hydroxy-5-benzyloxyphenyl]-4-(3,4,5-trimethoxyphenyl) butan-1,4-dione A mixture of 1-[3-bromo-4-hydroxy-5-benzyloxyphenyl]-4-(3,4,5-trimethoxyphenyl)butan-1,4-dione (30 g, 56.7 mmol), 2-hydroxyethyl disulfide (30 mL, 244 mmol) and copper powder (30 g) in dry pyridine (200 mL) was heated with vigorous stirring under reflux and nitrogen overnight. The progress of the reaction was monitored by TLC (hexane-ethyl acetate; 1:1, v/v). After the reaction was complete, the mixture was filtered hot over celite and washed with dichloromethane. The filtrates were combined and evaporated to a residue, which was partitioned between dichloromethane and 2N HCl. The organic layer was washed with water, dried, and concentrated to a small volume and passed through a sintered funnel of silica gel (100 g). The product was eluted with dichloromethane and then hexane-ethyl acetate (1:1, v/v). Fractions containing the desired product were combined and evaporated to dryness, and the residue was dissolved in a small volume of dichloromethane. Ethyl ether was added and crystals were collected and dried : $R_f$ 0.23 (hexane-ethyl acetate; 1:2, v/v); NMR (CDCl$_3$) δ 3.07 (t, J=6.0 Hz, SCH$_2$), 3.41 (COCH$_2$CH$_2$CO), 3.71 (t, SCH$_2$$\underline{CH_2}$). 3.93 (s, 3 OCH$_3$), 5.18 (s. OCH$_2$C$_6$H$_5$), 7.30 (s, 2H, C$_4$ArH), 7.37–7.45 (OCH$_2$$\underline{C_6H_5}$), 7.61 & 7.87 (2 d, J=1.5 Hz, 2 H, C$_1$ArH). The mother liquor, which contained some product as indicated by TLC, was not pursued further.

STEP 16B: 1-[3-(2-Hydroxyethylsulfonyl)-4-hydroxy-5-benzyloxyphenyl]-4-(3,4,5-trimethoxyphenyl)-butan-1,4-dione 3-Chloroperbenzoic acid (80–85%; 8.5 g, 39.4 mmol) was added to a solution of 1-[3-(2-hydroxyethylthio)-4-hydroxy-5-benzyloxyphenyl]-4-(3,4,5-trimethoxyphenyl)butan -1,4-dione (9.4 g, 17.9 mmol) in dichloromethane (80 mL). The mixture was stirred at room temperature for 6 h, filtered, and the filtrate was concentrated to a small volume. Ethyl ether was added and crystals were collected and washed with Et$_2$O. $R_f$ 0.26 (chloroform-methanol; 9:1, v/v); NMR (CDCl$_3$) δ 3.44 (COCH$_2$CH$_2$CO), 3.64 (t, SO$\underline{CH_2}$), 4.08 (t, SOCH$_2$$\underline{CH_2}$), 3.94 (s, 3 OCH$_3$), 5.22 (s, O$\underline{CH_2}$C$_6$H$_5$), 7.30 (s, 2H, C$_4$ArH), 7.43 (OCH$_2$$\underline{C_6H_5}$), 7.87 & 8.20 (2 d, J=1.5 Hz, 2 H, C$_1$ArH).

Step 16C: 1-[3(2-Hydroxyethylsulfonyl)-4-n-propoxy-5-benzyloxyphenyl]-4-(3,4,5-trimethoxyphenyl)butan-1,4-dione n-Propyl bromide (1.63 mL, 17.8 mmol) was added to a solution of 1-[3-(2-hydroxyethylsulfonyl)-4-hydroxy-5-benzyloxyphenyl]-4-(3,4,5-trimethoxyphenyl)butan-1,4-dione (5.53 g, 9.91 mmol) in DMF (10 mL) containing postassium carbonate (2.74 g, 19.9 mmol). The mixture was stirred at 75° C. for 2 h, and partitioned between ethyl ether and water. The aqueous layer was re-extracted with ether (2 x) and ethyl acetate. The organic extracts were combined, dried, and evaporated to dryness. The residue was triturated with Et$_2$O to give crystals, which was washed with Et$_2$O containing a small volume of acetone. This material, $R_f$ 0.53 (hexane-ethyl acetate; 1:2, v/v), was used directly in the next experiment without further purification.

STEP 16D: 1-[3-(2-Hydroxyethylsulfonyl)-4-n-propoxy-5-benzyloxyphenyl]-4-(3,4,5-trimethoxyphenyl)butan-1,4-diol.

Sodium borohydride (0.66 g) was added to a suspension of 1-[3-(2-hydroxyethylsulfonyl)-4-propoxy-5-benzyloxyphenyl]-4-(3,4,5-trimethoxyphenyl) butan-1,4-dione (from previous experiment) in ethanol (125 mL), and the mixture was heated at 75° C. for 2 h. The solution was cooled and diluted with dichloromethane. It was then washed with 2.5 N HCl (2 x) and water, dried, and evaporated to a syrup, $R_f$ 0.11 (hexane-ethyl acetate., 1:1, v/v). This material was used directly in the next experiment without further purification.

STEP 16E: trans-2-[3-(2-Hydroxyethylsulfonyl)-4-n-propoxy-5-benzyloxyphenyl]-5-(3,4,5-trimethoxyphenyl)tetra-hydrofuran.

A solution of 1-[3-(2-hydroxyethylsulfonyl)-4-n-propoxy-5-benzyloxyphenyl]-4-(3,4,5-trimethoxyphenyl)butan-1,4-diol (from previous experiment) in chloroform (20 mL) was treated with 10% trifluroacetic acid (20 mL). The reaction was monitored by TLC. After 1 h, anhydrous sodium carbonate was added, and the solid was filtered off and washed with chloroform. The solvent was evaporated and the residue was passed through a flash column of silica gel (hexane-ethyl acetate; 2:1, v/v). The cis- and trans-isomers were then separated by HPLC (hexane-ethyl acetate; 1:1, v/v). $R_f$ 0.33 (hexane-ethyl acetate; 1:1, v/v); NMR (CDCl$_3$) δ 0.98 (t, J=7.5 Hz, CH$_2$CH$_2$CH$_3$), 1.83 (m, CH$_2$ CH$_2$CH$_3$), 2.85 (t, J=6.5 Hz, OH), 3.67 (q, SO$_2$CH$_2$), 3.98 (q, SO$_2$CH$_2$CH$_2$), 4.17 (t, CH$_2$CH$_2$CH$_3$), 5.18 (s, CH$_2$C$_6$H$_5$), 6.63 (s, 2 H, C$_5$ArH).

STEP 16F: trans-2-[3-(2-Hydroxyethylsulfonyl)-4-n-propoxy-5-hydroxyphenyl]-5-(3,4,5-trimethoxyphenyl)-tetrahydrofuran.

A solution of trans-2-[3-(2-hydroxyethylsulfonyl)-4-n-propoxy-5-benzyloxyphenyl]-5-(3,4,5-trimethoxyphenyl)tetra-hydrofuran (440 mg) in ethyl acetate (6 mL) was hydrogenated over 10% palladium on charcoal (120 mg) at 45 psi for 1 h. The catalyst was filtered off and washed with ethyl acetate. The combined filtrates were evaporated to give the title compound $R_f$ 0.1 (hexane-ethyl acetate; 1:1, v/v); NMR (CDCl$_3$) δ 1.07 (t, CH$_2$CH$_2$CH$_3$), 3.60 (q, SO$_2$CH$_2$), 3.95 (q, SO$_2$CH$_2$CH$_2$), 3.84 (s, OCH$_3$), 3.88 (s, 2 OCH$_3$), 4.11 (t, CH$_2$CH$_2$CH$_3$), 5.13–5.25 (m, H-2 & H-5), 6.61 (s, 2 H, C$_5$ArH), 7.32 & 7.49 (2 d, J=2.0 Hz, C$_2$ArH).

STEP 16G: trans-2-[3-(2-Hydroxyethylsulfonyl)-4,5-di-n-propoxyphenyl]-5-(3,4,5-trimethoxyphenyl)tetrahydrofuran.

A mixture of trans-2-[3-(2-hydroxyethylsulfonyl)-4-n-propoxy-5-hydroxyphenyl]-5-(3,4,5-trimethoxyphenyl)-tetrahydrofuran (366 mg, 0.74 mmol), n-propyl bromide (0.12 mL, 1.33 mmol) and potassium carbonate (255 mg, 1.85 mmol) in DMF (3 mL) was heated at 75° C. for 1 h. The reaction mixture was cooled and partitioned between ethyl ether and water, and the aqueous layer was re-extracted with ether (2 x). The organic extracts were combined, dried, and evaporated to dryness. The residue was purified by chromatography to give the title compound: $R_f$ 0.43 (hexane-ethyl acetate; 1:2, v/v); NMR (CDCl$_3$) δ 1.05 & 1.09 (2 t, J=7.5 Hz, 2 CH$_2$CH$_2$CH$_3$), 2.85 (t, J=6.5 Hz, OH), 3.65 (m, SO$_2$CH$_2$), 3.95 (m, SO$_2$CH$_2$CH$_2$); 4.03 & 4.15 (2 t. J=6.5 Hz, 2 CH$_2$CH$_2$CH$_3$), 6.63 (s, 2 H, C$_5$ArH), 7.27 & 7.49 (2 d, J=1.5 Hz, C$_2$ArH).

STEP 16H: trans-2-[3-(2-O-Methanesulfonylethylsulfonyl)-4,5-di-n-propoxyphenyl]-5-(3,4,5-trimethoxyphenyl)tetrahydrofuran.

Methanesulfonyl chloride (0.097 mL, 1.25 mmol) was added to a solution of trans-2-[3-(2-hydroxyethylsulfonyl)- 4,5-di-n-propoxyphenyl]-5-(3,4,5-trimethoxyphenyl) tetrahydrofuran (338 mg, 0.63 mmol) in dichloromethane (3 mL) and pyridine (1.3 mL). The reaction mixture was stirred at room temperature for 2 h, and worked up as usual to give a syrup (387 mg), $R_f$ 0.52 (hexane-ethyl acetate; 1:2, v/v). This material was used directly in the next experiment without further purification.

STEP 16I: trans-2-(3-Vinylsulfonyl-4,5-di-n-propoxyphenyl)-5-(3,4,5-trimethoxyphenyl)tetrahydrofuran.

A solution of trans-2-[3-(2-O-methanesulfonyl-ethylsulfonyl)-4,5-di-n-propoxyphenyl]-5-(3,4,5-trimethoxyphenyl)tetrahydrofuran (387 mg, from previous experiment) in dichloromethane (5 mL) was treated with triethylamine (0.24 mL) for 30 min at room temperature. The solution was evaporated to a residue, which was purified by flash column chromatography (hexane-ethyl acetate; 3:1, v/v). The title compound had $R_f$ 0.38 (hexane-ethyl acetate; 1:1, v/v); NMR (CDCl$_3$) δ 1.06 & 1.09 (2 t, J=7.5 Hz, 2 CH$_2$CH$_2$CH$_3$), 4.01 & 4.15 (2 t, J=6.5 Hz, J=7.0 Hz, 2 CH$_2$CH$_2$CH$_3$). 5.16–5.27 (m, H-2 & H-5). 6.03 & 6.46 (2 d, J=10.0 Hz, J=17.0 Hz, SO$_2$CH=CH$_2$), 6.64 (s, 2 H, C$_5$ArH), 7.04 (2 d, SO$_2$CH=CH$_2$), 7.24 & 7.51 (2 d, J=1.5 Hz, C$_2$ArH).

STEP 16J: trans-2-[3-(2-N-Methylaminoethylsulfonyl)-4,5-di-n-propoxyphenyl]-5-(3,4,5-trimethoxyphenyl)tetrahydrofuran.

A solution of trans-2-(3-vinylsulfonyl-4,5-di-n-propoxyphenyl)-5-(3,4,5-trimethoxyphenyl) tetrahydrofuran (27 mg, 0.05 mmol) and aq. methylamine (40%, 0.02 mL) in acetonitrile (3 mL) was kept at room temperature for 1 h and evaporated to dryness. Purification by preparative TLC (CHCl$_3$ MeOH; 95:5, v/v) gave the title compound $R_f$ 0.42; MS, m/z 552 (M+1)$^+$; NMR (CDCl$_3$) δ 1.05 & 1.09 (2 t, J=7.5 Hz, 2 CH$_2$CH$_2$CH$_3$), 2.43 (s, NHCH$_3$), 2.99 (t, SO$_2$CH$_2$CH$_2$), 3.63 (t, SO$_2$CH$_2$CH$_2$), 3.86 (s, OCH$_3$), 3.91 (s, 2 OCH$_3$), 4.02 & 4.14 (2 t, J=6.5 Hz, 2 CH$_2$CH$_2$CH$_3$), 5.17–5.26 (m, H-2 & H-5). 6.64 (s, 2 H, C$_5$ArH), 7.28 & 7.48 (2 d, J=1.5 Hz, 2 H, C$_2$ArH).

EXAMPLE 17 trans-2-[3-(2-N,N-Dimethylaminoethylsulfonyl)-4,5-di-n-propoxyphenyl]-5-(3,4,5-trimethoxyphenyl)tetrayhydrofuran A solution of trans-2-(3-vinylsulfonyl-4,5-di-n-propoxyphenyl)-5-(3,4,5-trimethoxyphenyl)tetrahydrofuran (30 mg, 0.06 mmol) and aq. methylamine (40%, 0.03 mL) in acetonitrile (3 mL) was kept at room temperature for 6 h and evaporated to dryness. Purification by preparative TLC (CHCl$_3$-MeOH; 95:5, v/v) gave the title compound $R_f$ 0.29: MS, m/z 566 (M+1)$^+$; NMR (CDCl$_3$) δ 1.05 & 1.09 (2 t, J=7.5 Hz, 2 CH$_2$CH$_2$CH$_3$), 2.22 [s, N(CH$_3$)$_2$], 2.73 (q, SO$_2$CH$_2$CH$_2$), 3.60 (q, SO$_2$CH$_2$CH$_2$), 3.86 (s, OCH$_3$), 3.89 (s, 2 OCH$_3$), 4.02 & 4.15 (2 t, 2 CH$_2$CH$_2$CH$_3$), 5.16–5.28 (m, H-2 & H-5), 6.63 (s, 2 H, C$_5$ArH), 7.26 & 7.46 (2 d, 2 H, C$_2$ArH).

EXAMPLE 18 trans-2-[3-(2-Aminoethylsulfonyl)-4,5-dipropoxyphenyl]-5-(3,4,5-trimethoxyphenyl)tetrahydrofuran.

Ammonia was bubbled into a solution of trans-2-(3-vinylsulfonyl-4,5-dipropoxyphenyl)-5-(3,4,5-trimethoxy-phenyl)tetrahydrofuran (30 mg, 0.06 mmol) at 0.5° C. for 3 min in acetonitrile (3 mL). The solution was then heated at 65° C. in a pressure bottle overnight, cooled, and evaporated to dryness. Purification by preparative TLC (CHCl$_3$-MeOH; 95:5, v/v) gave the title compound MS, m/z 538 (M+1)$^+$; R$_f$ 0.27; NMR (CDCl$_3$) δ 1.05 & 1.09 (2 t J=7.5 Hz, 2 CH$_2$CH$_2$CH$_3$), 3.58 (bt, SO$_2$CH$_2$CH$_2$), 4.02 & 4.14 (2 t, J=6.5 Hz, 2 CH$_2$CH$_2$CH$_3$), 5.16–5.28 (m, H-2 & H-5), 6.63 (s, 2 H, C$_5$ArH), 7.27 & 7.48 (2 d, J=1.5 Hz, 2 H, C$_2$ArH).

Following the procedures outlined in Examples 16 and 17 were prepared the compounds 19 and 20.

EXAMPLE 19 trans-2-[3-(2-N-Ethylaminoethylsulfonyl)-4,5-dipropoxyphenyl]-5-(3,4,5-trimethoxyphenyl)tetrahydrofuran MS, m/z 566 (M+1)$^+$; NMR (CDCl$_3$) δ 1.05, 1.08 & 1.09 (3 t, 2 CH$_2$CH$_2$CH$_3$ & NHCH$_2$CH$_3$), 2.64 (q, NHCH$_2$CH$_3$), 3.03 (t, SO$_2$CH$_2$CH$_2$), 3.63 (t, SO$_2$CH$_2$CH$_2$), 3.86 (s, OCH$_3$), 3.89 (s, 2 OCH$_3$), 4.02 & 4.13 (2 t, 2 CH$_2$CH$_2$CH$_3$), 5.16–5.29 (m, H-2 & H-5), 6.63 (s, 2 H, C$_5$ArH), 7.26 & 7.46 (2 d, 2 H, C$_2$ArH).

EXAMPLE 20 trans-2-[3-(2-N-Propylaminoethylsulfonyl)-4,5-dipropoxyphenyl]-5-(3,4,5-trimethoxyphenyl)tetrahydrofuran MS, m/z 579 (M+1)$^+$; NMR (CDCl$_3$) δ 0.89 (t, J=7.5 Hz, NHCH$_2$CH$_2$CH$_3$), 1.05 & 1.09 (2 t, J=7.5 Hz, 2 CH$_2$CH$_2$CH$_3$), 1.46 ((q, NHCH$_2$CH$_2$CH$_3$), 2.56 (t, NHCH$_2$CH$_2$CH$_3$), 3.02 (t, SO$_2$CH$_2$CH$_2$), 3.63 (t, SO$_2$CH$_2$CH$_2$), 3.86 (s, OCH$_3$), 3.89 (s, 2 OCH$_3$), 4.02 & 4.14 (2 t, 2 CH$_2$CH$_2$CH$_3$), 5.16–5.29 (m, H-2 & H-5), 6.63 (s, 2 H, C$_5$ArH), 7.26 & 7.47 (2 d, 2 H, C$_2$ArH).

EXAMPLE 21 trans-2-[3-(2-N,N-Dimethylaminoethylsulfonyl)-4-n-propoxy-5-(3-hydroxypropoxy)phenyl]-5-(3,4,5-trimethoxyphenyl)tetrahydrofuran STEP 21A: trans-2-[3-(2-O-Methanesulfonylethylsulfonyl)-4-n-propoxy-5-benzyloxyphenyl]-5-(3,4,5-trimethoxyphenyl)tetra-hydrofuran.

Methanesulfonyl chloride (0.07 mL) was added to a solution of trans-2-[3-(2-hydroxy-ethylsulfonyl)-4-n-propoxy-5-benzyloxyphenyl]-5-(3,4,5-trimethoxyphenyl)tetrahydrofuran (250 mg, 0.43 mmol) in dichloromethane (3 mL) and pyridine (0.89 mL), and the mixture was stirred at room temperature for 2 h. The solution was diluted with dichloromethane and washed with 2 N HCl, aq. NaHCO$_3$ and water, dried, and evaporated to dryness. The R$_f$ of the product and the starting material were 0.43 and 0.33, respectively. The product was used directly in the next experiment without further purification.

STEP 21B: trans-2-[3-(2-N,N-Dimethylaminoethylsulfonyl)-4-propoxy-5-benzyloxyphenyl]-5-(3,4,5-trimethoxyphenyl)tetrahydrofuran.

A solution of trans-2-[3-(2-O-methane-sulfonylethylsulfomyl)-4-n-propoxy-5-benzyloxyphenyl]-5-(3,4,5-trimethoxyphenyl) tetrahydrofuran (from the previous experiment) in dichloromethane (3 mL) containing triethylamine (0.15 mL) was kept at room temperature for 30 min and evaporated to give trans-2-(3-vinylsulfonyl-4-propoxy-5-benzyloxyphenyl)]-5-(3,4,5-trimethoxyphenyl) tetrahydrofuran (faster mobility than the starting material): NMR (CDCl$_3$) δ 0 97 (t, CH$_2$CH$_2$CH$_3$), 3.85 (s, OCH$_3$), 3.88 (s, 2 OCH$_3$), 4.15 (t, CH$_2$CH$_2$CH$_3$), 5.15 (s, CH$_2$C$_6$H$_5$), 6.04 & 6.45 (2 d, J=10 Hz, J=17 Hz, SO$_2$CH=CH$_2$), 6.61 (s, 2 H, C$_5$ArH), 6.99 (2 d, SO$_2$CH=CH$_2$), 7.31 & 7.53 (2 d, 2 H, C$_2$ArH). This vinylsulfone was treated with aq. dimethylamine (40%, 0.22 mL) in acetonitrile (3 mL) at room temperature for 6 h. The solution was evaporated to dryness and the product was purified by preparative TLC (2% MeOH in CHCl$_3$). R$_f$ 0.22 (hexane-ethyl acetate; 1:2 v/v); NMR (CDCl$_3$) δ 1.0 (t, J=7.5 Hz, CH$_2$CH$_2$CH$_3$), 2.22 [s, N(CH$_3$)$_2$], 2.73 (q, SO$_2$CH$_2$CH$_2$), 3.62 (q, SO$_2$CH$_2$CH$_2$), 3.86 (s, OCH$_3$), 4.90 (s, 2 OCH$_3$), 4.17 (t, CH$_2$CH$_2$CH$_3$), 5.18 (q, CH$_2$C$_6$H$_5$), 5.12–5.29 (m H-2 & H-5), 6.63 (s, 2 H, C$_5$ArH).

STEP 21C: trans-2-[3-(2-N,N-Dimethylaminoethylsulfonyl)-4-n-propoxy-5-hydroxyphenyl]-5-(3,4,5-trimethoxyphenyl)tetrahydrofuran.

A solution of trans-2-[3-(2-N,N-dimethylaminoethylsulfonyl)-4-n-propoxy-5-benzyloxyphenyl]-5-(3,4,5-trimethoxyphenyl)tetrahydrofuran (178 mg, 0.29 mmol) in ethyl acetate (3 mL) was hydrogenated over 10% palladium-on-charcoal (53 mg) at 45 psi for 3 h. The catalyst was filtered off and washed with ethyl acetate. The filtrates were combined and evaporated to give the title compound R$_f$ 0.08 (hexane-ethyl acetate 1:2, v/v). NMR (CDCl$_3$) δ 1.04 (t, J=7.5 Hz, CH$_2$CH$_2$CH$_3$), 2.26 [s, N(CH$_3$)$_2$], 2.75 (m SO$_2$CH$_2$CH$_2$), 3.57 (m, SO$_2$CH$_2$CH$_2$), 3.86 (s, OCH$_3$), 3.88 (s, 2 OCH$_3$), 4.10 (t, 6.5 Hz, CH$_2$CH$_2$CH$_3$), 5.15–5.25 (m, H-2 & H-5), 6.63 (s, 2 H, C$_5$ArH), 7.25 & 7.44 (2 d, J=1.5 Hz, 2 H, C$_2$ArH).

STEP 21E: trans-2-[3-(2-N,N-Dimethylaminoethylsulfonyl)-4-n-propoxy-5-(3-hydroxypropoxy)phenyl]-5-(3,4,5-trimethoxyphenyl)tetrahydrofuran.

A mixture of trans-2-[3-(2-N,N-dimethylaminoethylsulfonyl)-4-n-propoxy-5-hydroxyphenyl]-5-( 3,4,5-trimethoxyphenyl) tetrahydrofuran (145 mg, 0.28 mmol), 3-bromopropanol (0.045 mL, 0.5 mmol) and cesium carbonate (226 mg, 0.69 mmol) in DMF (3 mL) was stirred at room temperature overnight. Ethyl ether and water were added and the aqueous layer was re-extracted with ether (2 x). The organic extracts were combined, dried, and evaporated to a syrup, which was purified by preparative TLC (CHCl$_3$ MeOH; 95:5, v/v) to give the title compound R$_f$ 0.27 (R$_f$ of s.m. 0.29); MS, m/z 582 (M+1)$^+$; NMR (CDCl$_3$) δ 1.05 (t, J=7.5 Hz, CH$_2$CH$_2$CH$_3$), 1.87 (m, CH$_2$CH$_2$CH$_3$), 2.11 (t, CH$_2$CH$_2$CH$_2$OH), 2.21 [s, N(CH$_3$)$_2$], 2.73 (q, SO$_2$CH$_2$CH$_2$), 3.59, (q, SO$_2$CH$_2$CH$_2$), 3.85 (s, OCH$_3$), 3.88 (s, 2 OCH$_3$), 4.12 (t, CH$_2$CH$_2$CH$_3$), 4.22 (t, CH$_2$CH$_2$CH$_2$OH), 5.12–5.28 (m, H-2 & H-5), 6.3 (s, 2 H, C$_5$ArH), 7.30 & 7.47 (2 d, J=1.5 Hz, 2 H, C$_2$ArH).

EXAMPLE 22 trans-2-[3-(2-Hydroxyethylsulfonyl)-4-n-propoxy-5-(2-oxo-propoxy)phenyl]-5-(3,4,5-trimethoxy-phenyl)tetrahydrofuran A mixture of trans-2-[3-(2-hydroxyethylsulfonyl)-4-n-propoxy-5-hydroxyphenyl]-5-(3,4,5-trimethoxyphenyl)-tetrahydrofuran (183 mg, 0.37 mmol), chloroacetone (0.033 mL, 0.41 mmol) and potassium carbonate (162 mg, 1.17 mmol) in DMF (3 mL) was stirred at room temperature overnight. Ethyl ether and water were added and the aqueous layer was re-extracted with ether (2 x). The organic extracts were combined, dried, and evaporated to a syrup, which was purified by preparative TLC (hexane-ethyl acetate; 1:2, v/v) to give the title compound $R_f$ 0.33; NMR (CDCl$_3$) δ 1.06 (t, CH$_2$CH$_2$CH$_3$), 2.33 (s, CH$_2$COCH$_3$), 3.66 (q, SO$_2$CH$_2$CH$_2$), 3.97 (b, SO$_2$CH$_2$CH$_2$) 4.20 (t, CH$_2$CH$_2$CH$_3$), 4.68 (s, CH$_2$COCH$_3$), 5.12-5.28 (m, H-2 & H-5), 6.62 (s, 2 H, C$_5$ArH), 7.17 & 7.56 (2 d, 2 H, C$_2$ArH).

EXAMPLE 24 trans-2-[3-(2-N,N-Dimethylaminoethyl-sulfonyl)-4-n-propoxy-5-(2-oxo-propoxyphenyl]-5-(3,4,5-trimethoxyphenyl)tetrahydrofuran Methanesulfonyl chloride (0.027 mL, 0.35 mmol) was added to a solution of trans-2-[3-(2-hydroxyethylsulfonyl)-4-n-propxy-5-(2-oxo-propoxy)phenyl]-5-(3,4,5-trimethoxy-phenyl)tetrahydrofuran (96 mg, 0.17 mmol) in dichloromethane (2 mL) and pyridine (0.37 mL). The mixture was stirred at room temperature for 2 h worked-up in the normal manner to give the mesylate. This material was treated with triethylamine (0.07 mL) in dichloromethane (3 mL) to yield trans-2-[3-vinyl-sulfonyl-4-n-propoxy-5-(2-oxo-propoxy)phenyl]-5-(3,4,5-trimethoxyphenyl)tetrahydrofuran: $R_f$ 0.40 (hexane-ethyl acetate; 1:1 v/v); NMR (CDCl$_3$) δ 1.06 (t, J=7.5 Hz, CH$_2$CH$_2$CH$_3$) 2.34 (s, CH$_2$COCH$_3$). 3.86 (s OCH$_3$), 3.89 (s, 2 OCH$_3$), 4.20 (t, J=6.5 Hz. CH$_2$CH$_2$CH$_3$), 4.66 (s, CH$_2$COCH$_3$). 5.13-5.26 (m, H-2 & H-5), 6.07 & 6.47 (2 d, J=9.5 Hz, J=16.5 Hz, SO$_2$CH=CH$_2$), 6.61 (s, 2 H, C$_5$ArH), 7.03 (2 d, SO$_2$CH=CH$_2$), 7.14 & 7.58 (2 d, J=1.5 Hz, 2 H, C$_2$ArH). The above vinyl sulfone was treated with aq. dimethylamine (40%, 0.19 mL) in acetonitrile at room temperature for 3 h. The solution was evaporated to dryness and the residue was purified by preparative TLC (CHCl$_3$-MeOH; 95:5, v/v) to give the title compound $R_f$ 0.39; MS, m/z 580 (M+1)$^+$; NMR (CDCl$_3$) δ 1.07 (t, J=7.5 Hz, CH$_2$CH$_2$CH$_3$), 1.91 (m, CH$_2$CH$_2$CH$_3$), 1.92 & 2.48 (2 m, H-3 & H-4), 2.21 [s, N(CH$_3$)$_2$], 2.33 (s, CH$_2$COCH$_3$), 2.72 (q, SO$_2$CH$_2$CH$_2$), 3.60 (q, SO$_2$CH$_2$CH$_2$), 3.85 (s, OCH$_3$), 3.88 (s, 2 OCH$_3$), 4.20 (t, J=6.5 Hz, CH$_2$CH$_2$CH$_3$), 4.67 (s, CH$_2$COCH$_3$), 5.12-5.29 (m, H-2 & H-5), 6.62 (s, 2 H, C$_5$ArH), 7.16-7.54 (2 d, J=1.5 Hz, 2 H, C$_2$ArH).

EXAMPLE 25 trans-2-[3-(2-N,N-Dimethylaminoethylsulfonyl)-4-n-propoxy-5-(2-hydroxypropoxy)phenyl]-5-(3,4,5-trimethoxyphenyl)tetrahydrofuran A mixture of trans-2-[3-(2-N,N-dimethylaminoethylsulfonyl)-4-n-propoxy-5-(2-oxo-propoxy)phenyl]-5-(3,4,5-trimethoxyphenyl)tetrahydrofuran (40 mg, 0.07 mmol) and sodium borohydride (5 mg, 0.13 mmol) in ethanol (5 mL) was heated at 70° C. for 1 h. The solution was cooled and dichloromethane and water were added. The organic layer was separated and washed with brine, dried, and evaporated to dryness.

The residue was purified by preparative TLC (CHCl$_3$-MeOH; 95:5, v/v) to give the title compound NMR (CDCl$_3$) δ 1.06 (t, J=7.5 Hz, CH$_2$CH$_2$CH$_3$), 1.32 (2 d, J=6.0 Hz, J=0.5 Hz, CH$_2$CHOHCH$_3$), 1.88 (m, CH$_2$CH$_2$CH$_3$), 2.22 [s, N(CH$_3$)$_2$], 2.73 (q, SO$_2$CH$_2$CH$_2$), 3.59 (q, SO$_2$CH$_2$CH$_2$), 3.86 (s, OCH$_3$), 3.89 (s, 2 OCH$_3$), 4.14 (t, J=6.5 Hz, CH$_2$CH$_2$CH$_3$), 5.15-5.26 (m, H-2 & H-5), 6.63 (s, 2 H, C$_5$ArH), 7.30 & 7.51 (2 b, 2 H, C$_2$ArH).

EXAMPLE 26

Salts of the title compound of Example 5 are prepared as follows:

(−)-trans-(2S,5S)-[3-(2-Oxopropylsulfonyl)-4-n-propoxy-5-[3-(phosphonooxy)propoxy]phenyl]-5-(3,4,5-trimethoxyphenyl)tetrahydrofuran monopotassium salt A solution of (−)-trans-(2S,5S)-[3-(2-oxopropylsulfonyl)-4-n-propoxy-5-(3-dibenzyloxyphosphorylpropoxy)-phenyl]-5-(3,4,5-trimethoxyphenyl)tetrahydrofuran (STEP 5D; 10.75 g, 1.3 mmol) in methanol (200 mL) containing KHCO$_3$ (1.3 g, 1.3 mmol; in 4 mL of H$_2$O) was hydrogenated over 10% palladium on-charcoal (1.2 g.) at 40 psi for 1 h. The solid was filtered off through Celite and washed with water and the filtrate was concentrated to a small volume of water and lyophilized to give the monopotassium salt (8.7 g, 98%) This material was crystallized from aqueous isopropanol as follows: isopropanol (90%, 50 mL) was added to the monopotassium salt (3.0 g) and then water (about 1.0 mL) was added until dissolution. The monopotassium salt was allowed to crystallize at 4° C. for 24 h, filtered cold and immediately washed with isopropanol to give the crystalline monopotassium salt (1.0 g); softened at 104° C., mp 119°-125° C.; NMR (CDCl$_3$) d 0.98 (t, CH$_2$CH$_2$CH$_3$), 2.31 (s, SO$_2$CH$_2$COCH$_3$), 4.42 (s, SO$_2$CH$_2$COCH$_3$), 5.16 (m, H-2 & H-5), 6.6 (s, C$_2$ArH), 7.28 & 7.44 (d, C$_5$ArH). Anal. for C$_{28}$H$_{38}$O$_{13}$KPS.H$_2$O:

Calc.: C 47.86; H 5.74; K 5.56; P 4.41.
Found: C 47.64; H 5.68; K 5.67; P 4.41.

The Monosodium and Monolithium Salts of (−)-trans-(2S,5S)-[3-(2-Oxopropylsulfonyl)-4-n-propoxy-5-[3-(phosphonooxy)propyl]phenyl]-5-(3,4,5-trimethoxyphenyl)tetrahydrofuran were prepared similarly as for the monopotassium salt by performing the hydrogenolysis in the presence of NaHCO$_3$ and LiHCO$_3$, respectively.

(−)-trans-(2S,5S)-[3-(2-oxopropylsulfonyl)-4-n-propoxy-5-[3-(phosphonooxy)propyl]phenyl]-5-(3,4,5-trimethoxyphenyl)tetrahydrofuran monoammonium salt A solution of (−)-trans-(2S,5S)-[3-(2-oxopropylsulfonyl)-4-n-propoxy-5-(3-dibenzyloxyphosphoryl-propoxy)phenyl]-5-(3,4,5-trimethoxyphenyl)tetrahydrofuran (10.75 g, 1.3 mmol) in methanol (200 mL) and ammonium hydroxide (5 mL) was hydrogenated over 10% palladium-on charcoal (1.2 g) at 40 psi for 1 h. The catalyst was filtered off through Celite and washed with water and the filtrate was concentrated to a small volume of water and lyophilized to give the ammonium salt (7.5 g).

(−)-trans-(2S,5S)-[3-(2-Oxopropylsulfonyl)-4-n-propoxy-5-[3-(phosphonooxy)propoxy]phenyl]-5-(3,4,5-trimethoxyphenyl)tetrahydrofuran mono-tert-amine salts The appropriate tert-amine (1.3 mmol) was added to a solution of (−)-trans-(2S,5S)-[3-(2-oxopropylsulfonyl)-4-n-propoxy-5-(3-dibenzyloxyphosphorylpropoxy)-phenyl]-5-(3,4,5-trimethoxyphenyl)tetrahydrofuran (10.75 g, 1.3 mmol) in ethyl acetate or methanol (200 mL) and the mixture was hydrogenated over 10% palladium on-charcoal (1.2 g.) at 40 psi for 1 h. The catalyst was filtered off through Celite and the filtrate was concentrated to dryness. Water was added and the solution was lyophilized to give the tert amine salt.

(−)-trans-(2S,5S)-[3-(2-Oxopropylsulfonyl)-4-n-propoxy-5-[3-(phosphonooxy)propoxy]phenyl]-5-(3,4,5-trimethoxyphenyl)tetrahydrofuran mono alkyl or mono dialkylamine Salts The monotriethylamine (1.0 mol) was passed through a column of resin (H+) and treated with primary and secondary amines (1.0 mol) to give the mono alkyl or mono dialkylamine salts.

(−)-trans-(2S,5S)-[3-(2-Oxopropylsulfonyl)-4-n-propoxy-5-[3-(phosphonooxy)propoxy]phenyl]-5-(3,4,5-trimethoxyphenyl)tetrahydrofuran dimetallic salts (−)-trans-(2S,5S)-[3-(2-Oxopropylsulfonyl)-4-n-propoxy-5-[3-(phosphonooxy)propoxy]phenyl]-5-(3,4,5-trimethoxyphenyl)tetrahydrofuran monotriethylamine salt (1.0 mol) was treated with monocationic hydroxide (2.0 mol) or dicationic hydroxide (1.0 mol) in aqueous alcohol to give dimetallic salts.

(−)-trans-(2S,5S)-[3-(2-Oxopropylsulfonyl)-4-n-propoxy-5-[3-(phosphonooxy)propoxy]phenyl]-5-(3,4,5-trimethoxyphenyl)tetrahydrofuran magnesium salt A solution of Mg(OAc)$_2$.4 H$_2$O (43 mg, 0.2 mmol) in methanol or water (3 mL) was added dropwise to a stirred solution of the monopotassium salt (137 mg, 0.2 mmol) in H$_2$O (1 mL). The clear solution slowly deposited solid. After 2 h, the solid (120 mg) was filtered and dried.

The barium calcium, and zinc salts of (−)-trans-(2S,5S)-[3-(2-Oxopropylsulfonyl)-4-n-propoxy-5-[3-phosphonooxy)propoxyl]phenyl]-5-(3,4,5-trimethoxyphenyl)tetrahydrofuran were prepared similarly as for the magnsium salt by using appropriate metallic acetates.

The potassium ornithine Salt of (−)-trans-(2S,5S)-[3-(2-Oxopropylsulfonyl)-4-n-propoxy-5-[3-(phosphonooxy)propoxyl]phenyl]-5-(3,4,5-trimethoxyphenyl)tetrahydrofuran A solution of the monopotassium salt (1.54 g) and L-ornithine hydrochloride (0.38 g) in water (5 mL) was evaporated in vacuo at 45° C. to dryness. Methanol (80 mL) was added and the mixture was shaken and warmed on a water bath. Insoluble solid was filtered off and the filtrate was evaporated to a residue. Aqueous isopropanol (90%, 100 mL) was added and the mixture was warmed on a water bath and allowed to cool to room temperature. Insoluble solid was filtered off and the filtrate was kept at 0°–5° C. for 2 d. Crystals (652 mg) were filtered and dried at 60° C. in high vacuo overnight. Second crop of crystals (313 mg) were also collected from the mother liquor. The ornithine salt has the following physical constants: softened at 98° C., mp 107°–112° C. (d); [a]$_D$ −47° (c, 1.07, H$_2$O); NMR (D$_2$O-DSS) d 1.03 (t, J=7.5 Hz, CH$_2$CH$_2$CH$_3$), 1.17 [d, J=6.0 Hz, (CH$_3$)$_2$CHOH], 1.84 (m, CH$_2$CH$_2$CH$_3$), 2.17 (t, J=6.0 Hz, CH$_2$CH$_2$CH$_2$OP), 2.30 (s, CH$_3$CO), 3.05 (t, J=7.5 Hz, H$_3$N+CH$_2$CH$_2$CH$_3$), 3.77 (s, OCH$_3$), 3.85 (s, 2 OCH$_3$), 5.18–5.31 (m, H-2 & H-5), 6.77 (s, C$_5$ArH), 7.45 (b, C$_2$ArH); IR (KBr) n 1720 cm$^{-1}$ (C=O), 1595 (COO$^-$); UV (H$_2$O) 1$_{max}$ 297 nm (e 68.4), 207 nm (e 1114); HPLC (C$_{18}$ reversed-phase) rt 10.6 min (identical to monoK+; 22–52% MeCN in H$_2$O); HPTLC (silica gel) R$_f$ 0.46 (i-propanol-NH$_4$OH, 67:33; v/v), R$_f$ 0.15 (L-ornithine).

Anal. for C$_{61}$H$_{89}$KN$_2$O$_{28}$P$_2$S$_2$ (1463.5):
Calc.: C 50.06; H 6.13; K 2.67; N 1.91; P, 4.23; S, 4.38.
Found: C 49.80., H 6.23; K 2.33; N 1.70., P 4.25.

The Lysine Salt of (−)-trans-(2S,5S)-[3-(2-Oxopropylsulfonyl)-4-n-propoxy-5-[3-(phosponooxy)-propoxyl]phenyl]-5-(3,4,5-trimethoxyphenyl)tetrahydrofuran was prepared from the monopotassium salt and L-lysine hydrochloride similarly as described for the ornithine salt. The lysine salt was crystallized from 90% isopropanol. It was birefringent by optical microscopy and had MS (FAB) m/z 793 (M+H).

The Arginine and Other Amino Acids Salts of (−)-trans-(2S,5S)-[3-(2-Oxopropylsulfonyl)-4-n-propoxy-5-[3-(phosphonooxy)propoxyl]phenyl]-5-(3,4,5-trimethoxyphenyl)tetrahydrofuran can be prepared similarly as for the ornithine salt using L-arginine hydrochloride and other amino acid hydrochlorides.

What is claimed is:

1. A compound of the following structural formula

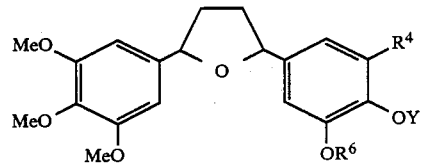

or a pharmaceutically acceptable salt thereof wherein:
R$^4$ is S(O)$_n$ R$^2$, in which n is 0, 1 or 2, and
R$^2$ is selected from the group consisting of
  (a) C$_{2-6}$alkyl,
  (b) Substituted C$_{1-6}$alkyl wherein the substituent is selected from the group consisting of hydroxy, amino, N—C$_{1-4}$alkylamino, and N,N-di-C$_{1-4}$alkylamino, and
  (c) C$_{1-6}$alkylcarbonyl-C$_{1-6}$alkyl;
Y is selected from the group consisting of
  (a) C$_{1-12}$alkyl
  (b) C$_{1-6}$hydroxyalkyl,
  (c) C$_{1-6}$alkylcarbonyl C$_{1-6}$alkyl, and
  (d) unsubstituted, mono, or di substituted amino C$_{1-6}$alkyl where the substituent is C$_{1-6}$alkyl;
R$^6$ is selected from the group consisting of
  (a) substituted C$_{1-6}$alkyl wherein the substituent is selected from the group consisting of hydroxy, amino, N-C$_{1-4}$alkylamino, N,N-di-C$_{1-4}$ alkylamino, and —O—R$^{10}$, wherein R$^{10}$ is
    (1) —PO$_2$(OH)$^-$ M$^+$ wherein M$^+$ is a pharmaceutically acceptable monovalent cation,
    (2) —SO$_3^-$ M$^+$, or
    (3) —C(O)(CH$_2$)$_2$—CO$_2^-$ M$^+$,
  (b) C$_{1-6}$alkylcarbonyl-C$_{1-6}$alkyl, or
  (c) C$_{1-6}$carboxyalkyl.

2. A compound of claim 1 wherein the substituents at positions 2 and 5 of the tetrahydrofuran are in a trans relationship to one another.

3. A compound according to claim 2 wherein n is 2, and R$^2$ is selected from the group consisting of:
  (a) Substituted C$_{1-6}$alkyl wherein the substituent is selected from the group consisting of hydroxy, amino, N—C$_{1-4}$alkylamino, and N,N-di-C$_{1-4}$alkylamino, and (b) C$_{1-6}$alkylcarbonyl C$_{1-6}$alkyl; and Y is (a) C$_{1-6}$alkyl, or (b) C$_{1-4}$alkylcarbonyl C$_{1-4}$alkyl.

4. A compound according to claim 3 wherein R$^6$ is selected from the group consisting of (a) substituted C$_{1-6}$alkyl wherein the substituent is selected from the group consisting of hydroxy, amino, N—C$_{1-4}$alkylamino, N,N-di-C$_{1-4}$alkylamino, and —O—R$^{10}$, wherein R$^{10}$ is (1) —PO$_2$(OH)$^-$ M$^+$ wherein M$^+$, (2) —SO$_3^-$ M$^+$, or (3) —C(O)(CH$_2$)$_2$—CO$_2^-$ M$^+$, and (b) C$_{1-6}$alkylcarbonyl-C$_{1-6}$alkyl.

5. A compound according to claim 4 wherein Y is n-propyl or 2-oxopropyl.

6. A compound of claim 5 which is (a) trans-2-[3-(2-Oxopropylsulfonyl)-4-n-propoxy-5-(3-(N,N-dimethylamino)-n-propoxy)phenyl]-5-(3,4,5-trimethoxyphenyl)tetrahydrofuran, (b) trans-2-[3-(2-Oxopropylsulfonyl)-4-n-propoxy-5-(3-hydroxy-n-propoxy)phenyl]-5-(3,4,5-trimethoxyphenyl)tetrahydrofuran, (c) trans-[3-(2-Oxopropylsulfonyl)-4-n-propoxy-5-(3-(phosphonooxy)propoxy)phenyl]-5-(3,4,5-trimethoxyphenyl)tetrahydrofuran, (d) trans-2-[3-(2-Oxopropylsulfonyl)-4-n-propoxy-5-(2-oxopropoxy)phenyl]-5-(3,4,5-trimethoxyphenyl)tetrahydrofuran, (e) trans-2-[3-(2-hydroxy-n-propylsulfonyl)-4-n-propoxy-5-(3-hydroxy-n-propoxy)phenyl]-5-(3,4,5-trimethoxyphenyl)tetrahydrofuran, (f) trans-2-[3-(2-hydroxy-n-propylsulfonyl)-4-n-propoxy-5-(2-oxopropoxy)phenyl]-5-(3,4,5-trimethoxyphenyl)tetrahydrofuran, (g) trans-2-[3 (2-Amino-n-propyl sulfonyl)-4-n-propoxy-5-(3-hydroxy-n-propoxy)phenyl]-5-(3,4,5-trimethoxyphenyl)tetrahydrofuran, (h) trans-2-[3-(2-N-Methylamino-n-propylsulfonyl)-4-n-propoxy-5-(3-hydroxy-n-propoxy)phenyl]-5-(3,4,5-trimethoxyphenyl)tetrahydrofuran, (i) trans-2-[3-(2-N,N-dimethylaminopropylsulfonyl)-4-n-propoxy-5-(3-hydroxy-n-propoxy)phenyl]-5-(3,4,5-trimethoxyphenyl)tetrahydrofuran, (j) trans-2-[3-(2-N-Ethylamino-n-propylsulfonyl)-4-n-propoxy-5-(3-hydroxy-n-propoxy)phenyl]-5-(3,4,5-trimethoxyphenyl)tetrahydrofuran, (k) trans-2-[3-(2-N-Methylaminoethylsulfonyl)-4,5-di-n-propoxyphenyl]-5-(3,4,5-trimethoxyphenyl)tetrahydrofuran, (l) trans-2-[3-(2-N,N-Dimethylaminoethylsulfonyl)-4,5-di-n-propoxyphenyl]-5-(3,4,5-trimethoxyphenyl)tetrahydrofuran, (m) trans-2-[3-(2-Aminoethylsulfonyl)-4,5-di-n-propoxyphenyl]-5-(3,4,5-trimethoxyphenyl)tetrahydrofuran, (n) trans-2-[3-(2-N-Ethylaminoethylsulfonyl)-4,5-di-n-propoxyphenyl]-5-(3,4,5-trimethoxyphenyl)tetrahydrofuran, (o) trans-2-[3-(2-N-propylaminoethylsulfonyl)-4,5-di-n-propoxyphenyl]-5-(3,4,5-trimethoxyphenyl)tetrahydrofuran, (p) trans-2-[3-(2 N,N-Dimethylaminoethylsulfonyl)-4-n-propoxy-5-(3-hydroxy-n-propoxy)phenyl]-5-(3,4,5-trimethoxyphenyl)tetrahydrofuran, (q) trans-2-[3-(2-N,N-Dimethylaminoethylsulfonyl)-4-n-propoxy-5-(2-oxopropoxyphenyl]-5-(3,4,5-trimethoxyphenyl)tetrahydrofuran, (r) trans-2 [3-(2-Hydroxyethylsulfonyl)-4-n-propoxy-5-(2-oxopropoxy)phenyl]-5-(3,4,5-trimethoxyphenyl)tetrahydrofuran, (s) trans-2-[3-(2-N,N Dimethylaminoethylsulfonyl)-4-n propoxy-5-(2 hydroxy-n-propoxy)phenyl]-5-(3,4,5-trimethoxyphenyl)tetrahydrofuran, or a stereochemical isomer thereof in the (2S,5S) configuration.

7. A compound of claim 6 which is (a) trans-2-[3-(2-Oxopropylsulfonyl)-4-n-propoxy-5-(3-hydroxy-n-propoxy)phenyl]-5-(3,4,5-trimethoxyphenyl)tetrahydrofuran, or (b) trans-2-[3-(2-hydroxy-n-propylsulfonyl)-4-n-propoxy-5-(3-hydroxy-n-propoxy)phenyl]-5-(3,4,5-trimethoxyphenyl)tetrahydrofuran.

8. A compound of claim 7 which is (2S,5S)-2-[3-(2-Oxopropylsulfonyl)-4-n-propoxy-5-(3-hydroxy-n-propoxy)phenyl]-5-(3,4,5-trimethoxyphenyl)tetrahydrofuran.

9. A compound of claim 6 which is (a) trans-2-[3-(2-Oxopropylsulfonyl)-4-n-propoxy-5-(3-phosphonooxy)propoxy)phenyl]-5-(3,4,5-trimethoxyphenyl)tetrahydrofuran, or (b) trans-2-[3-(2-hydroxy-n-propylsulfonyl)-4-n-propoxy-5-(3-hydroxy-n-propoxy)phenyl]-5-(3,4,5-trimethoxyphenyl)tetrahydrofuran.

10. A compound of claim 9 which is (a) (2S,5S)-2-[3-(2-Oxopropylsulfonyl)-4-n-propoxy-5-(3-(phosphonooxy)propoxy)phenyl]-5-(3,4,5-trimethoxyphenyl)tetrahydrofuran, or (b) (2S,5S)-2-[3-(2-hydroxy-n-propylsulfonyl)-4-n-propoxy5-(3-hydroxy-n-propoxy)phenyl]-5-(3,4,5-trimethoxyphenyl)tetrahydrofuran.

11. A pharmaceutical composition for antagonising the effects of PAF which comprises a nontoxic therapeutically effective amount of a compound according to claim 1 and a pharmaceutically acceptable carrier.

12. A composition of claim 11 in which the active agent is (a) trans-2-[3-(2-Oxopropylsulfonyl)-4-n-propoxy-5-(3-(N,N-dimethylamino)-n-propoxy)phenyl]-5-(3,4,5-trimethoxyphenyl)tetrahydrofuran, (b) trans-2-[3-(2-Oxopropylsulfonyl)-4-n-propoxy-5-(3-hydroxy-n-propoxy)phenyl]-5-(3,4,5-trimethoxyphenyl)tetrahydrofuran, (c) trans-2-[3-(2-Oxopropylsulfonyl)-4-n-propoxy-5-(3-(phosphonooxy)propoxy)phenyl]-5-(3,4,5-trimethoxyphenyl)tetrahydrofuran, (d) trans-2-[3-(2-Oxopropylsulfonyl)-4-n-propoxy-5-(2-oxopropoxy)phenyl]-5-(3,4,5-trimethoxyphenyl)tetrahydrofuran, (e) trans-2-[3-(2-hydroxy-n-propylsulfonyl)-4-n-propoxy-5-(3-hydroxy-n-propoxy)phenyl]-5-(3,4,5-trimethoxyphenyl)tetrahydrofuran, (f) trans-2-[3-(2-hydroxy-n-propylsulfonyl)-4-n-propoxy-5-(2-oxopropoxy)phenyl]-5-(3,4,5-trimethoxyphenyl)tetrahydrofuran, (g) trans-2-[3 (2-Amino-n-propyl sulfonyl)-4-n-propoxy-5-(3-hydroxy-n-propoxy)phenyl]-5-(3,4,5-trimethoxyphenyl)tetrahydrofuran, (h) trans-2-[3-(2-N-Methylamino-n-propylsulfonyl)-4-n-propoxy-5-(3-hydroxy-n-propoxy)phenyl]-5-(3,4,5-trimethoxyphenyl)tetrahydrofuran, (i) trans-2-[3-(2-N,N-dimethylaminopropylsulfonyl)-4-n-propoxy-5-(3-hydroxy-n-propoxy)phenyl]-5-(3,4,5-trimethoxyphenyl)tetrahydrofuran, (j) trans-2-[3-(2-N-Ethylamino-n-propylsulfonyl)-4-n-propoxy-5-(3-hydroxy-n-propoxy)phenyl]-5-(3,4,5-trimethoxyphenyl)tetrahydrofuran, (k) trans-2-[3-(2-N-Methylaminoethylsulfonyl)-4,5-di-n-propoxyphenyl]-5-(3,4,5-trimethoxyphenyl)tetrahydrofuran, (l) trans-2-[3-(2-N,N-Dimethylaminoethylsulfonyl)-4,5 di-n-propoxyphenyl]-5-(3,4,5-trimethoxyphenyl)tetrahydrofuran, (m) trans-2-[3-(2-Aminoethylsulfonyl)-4,5-di-n-propoxyphenyl]-5-(3,4,5-trimethoxyphenyl)tetrahydrofuran, (n) trans-2-[3-(2-N-Ethylaminoethylsulfonyl)-4,5-di-n-propoxyphenyl]-5-(3,4,5-trimethoxyphenyl)tetrahydrofuran, (o) trans-2-[3-(2-N propylaminoethylsulfonyl)-4,5-di-n-propoxyphenyl]-5-(3,4,5-trimethoxyphenyl)tetrahydrofuran, (p) trans-2-[3-(2 N,N-Dimethylaminoethylsulfonyl)-4-n-propoxy-5-(3-hydroxy-n-propoxy)phenyl]-5-(3,4,5-trimethoxyphenyl)tetrahydrofuran, (q) trans-2-[3-(2-N,N-Dimethylaminoethylsulfonyl)-4-n-propoxy-5-(2-oxopropoxyphenyl)-5-(3,4,5-trimethoxyphenyl)tetrahydrofuran, (r) trans-2 [3-(2-Hydroxyethylsulfonyl)-4-n-propoxy-5-(2-oxopropoxy)phenyl]-5-(3,4,5-trimethoxyphenyl)-tetrahydrofuran, or (s) trans-2-[3-(2-N,N Dimethylaminoethylsulfonyl)-4-n-propoxy-5-(2 hydroxy-n-propoxy)phenyl]-5-(3,4,5-trimethoxyphenyl)tetrahydrofuran.

13. A composition of claim 12 in which the active agent is in the (2S,5S) configuration.

14. A composition of claim 13 in which the active agent is
(a) (2S,5S)-2-[3-(2-Oxopropylsulfonyl)-4-n-propoxy-5-(3-hydroxy-n-propoxy)phenyl]-5-(3,4,5-trimethoxyphenyl)tetrahydrofuran, or
(b) (2S,5S)-2-[3-(2-Oxopropylsulfonyl)-4-n-propoxy5-(3-(phosphonoxy)propoxy)phenyl]-5-(3,4,5-trimethoxyphenyl)tetrahydrofuran.

15. A method of antagonising the effects of PAF in a subject in need thereof which comprises administrating to said subject a nontoxic therapeutically effective amount of a compound according to claim 1.

16. A method of claim 15 in which the active agent is
(a) trans-2-[3-(2-Oxopropylsulfonyl)-4-n-propoxy-5-(3-(N,N-dimethylamino)-n-propoxy)phenyl]-5-(3,4,5-trimethoxyphenyl)tetrahydrofuran,
(b) trans-2-[3-(2-Oxopropylsulfonyl)-4-n-propoxy-5-(3-hydroxy-n-propoxy)phenyl]-5-(3,4,5-trimethoxyphenyl)tetrahydrofuran,
(c) trans-2-[3-(2-Oxopropylsulfonyl)-4-n-propoxy-5-(3-(phosphonooxy)propoxy)phenyl]-5-(3,4,5-trimethoxyphenyl)tetrahydrofuran,
(d) trans-2-[3-(2-Oxopropylsulfonyl)-4-n-propoxy-5-(2-oxopropoxy)phenyl]-5-(3,4,5-trimethoxyphenyl)tetrahydrofuran,
(e) trans-2-[3-(2-hydroxy-n-propylsulfonyl)-4-n-propoxy-5-(3-hydroxy-n-propoxy)phenyl]-5-(3,4,5-trimethoxyphenyl)tetrahydrofuran,
(f) trans-2-[3-(2-hydroxy-n-propylsulfonyl)-4-n-propoxy-5-(2-oxopropoxy)phenyl]-5-(3,4,5-trimethoxyphenyl)tetrahydrofuran,
(g) trans-2-[3 (2-Amino-n-propyl sulfonyl)-4-n-propoxy-5-(3-hydroxy-n-propoxy)phenyl]-5-(3,4,5-trimethoxyphenyl)tetrahydrofuran,
(h) trans-2-[3-(2-N-Methylamino-n-propylsulfonyl)-4-n-propoxy-5-(3-hydroxy-n-propoxy)phenyl]-5-(3,4,5-trimethoxyphenyl)tetrahydrofuran, (i) trans-2-[3-(2-N,N-dimethylaminopropylsulfonyl)-4-n-propoxy-5-(3-hydroxy-n-propoxy)phenyl]-5-(3,4,5-trimethoxyphenyl)tetrahydrofuran, (j) trans-2-[3-(2-N-Ethylamino-n-propylsulfonyl)-4-n-propoxy-5-(3-hydroxy-n-propoxy)phenyl]-5-(3,4,5-trimethoxyphenyl)tetrahydrofuran, (k) trans-2-[3-(2-N-Methylaminoethylsulfonyl)-4,5-di-n-propoxyphenyl]-5-(3,4,5-trimethoxyphenyl)tetrahydrofuran, (l) trans-2-[3-(2-N,N-Dimethylaminoethylsulfonyl)-4,5 di-n-propoxyphenyl]-5-(3,4,5-trimethoxyphenyl)tetrahydrofuran, (m) trans-2-[3-(2-Aminoethylsulfonyl)-4,5-di-n-propoxyphenyl]-5-(3,4,5-trimethoxyphenyl)tetrahydrofuran, (n) trans-2-[3-(2-N-Ethylaminoethylsulfonyl)-4,5-di-n-propoxyphenyl]-5-(3,4,5-trimethoxyphenyl)tetrahydrofuran, (o) trans-2-[3-(2-N-propylaminoethylsulfonyl)-4,5-di-n-propoxyphenyl]-5-(3,4,5-trimethoxyphenyl)tetrahydrofuran, (p) trans-2-[3-(2 N,N-Dimethylaminoethylsulfonyl)-4-n-propoxy-5-(3-hydroxy-n-propoxy)phenyl]-5-(3,4,5-trimethoxyphenyl)tetrahydrofuran, (q) trans-2-[3-(2-N,N-Dimethylaminoethylsulfonyl)-4-n-propoxy-5-(2-oxopropoxyphenyl)-5-(3,4,5-trimethoxyphenyl)tetrahydrofuran, (r) trans-2 [3-(2-Hydroxyethylsulfonyl)-4-n-propoxy-5-(2-oxo-propoxy)phenyl]-5-(3,4,5-trimethoxyphenyl)-tetrahydrofuran, or (s) trans-2-[3-(2-N,N Dimethylaminoethylsulfonyl)-4-n propoxy-5-(2 hydroxy-n-propoxy)phenyl]-5-(3,4,5-trimethoxyphenyl)tetrahydrofuran.

17. A method of claim 16 in which the active agent is in the (2S,5S) configuration.

18. A method of claim 17 in which the active agent is
(a) (2S,5S)-2-[3-(2-Oxopropylsulfonyl)-4-n-propoxy-5-(3-hydroxy-n-propoxy)phenyl]-5-(3,4,5-trimethoxyphenyl)tetrahydrofuran,
(b) (2S,5S)-2-[3-(2-Oxopropylsulfonyl)-4-n-propoxy-5-(3-(phosphonooxy)propoxy)phenyl]-5-(3,4,5-trimethoxyphenyl)tetrahydrofuran, or
(c) (2S,5S)-2-[3-(2-hydroxy-n-propylsulfonyl)-4-n-propoxy-5-(3-hydroxy-n-propoxy)phenyl]-5-(3,4,5-trimethoxyphenyl)tetrahydrofuran.

19. A compound of claim 10 which is (2S,5S)-2-[3-((2S)-2-hydroxy-n-propylsulfonyl)-4-n-propoxy-5-(3-hydroxy-n-propoxy)phenyl]-5-(3,4,5-trimethoxyphenyl)tetrahydrofuran.

20. A compound of formula (I):

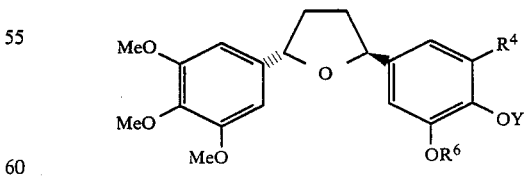

in the (2S,5S) configuration or a pharmaceutically acceptable salt thereof, wherein:
$R^4$ is $SO_2CH_2COCH_3$,
Y is $-CH_2CH_2CH_3$, and
$R^6$ is selected from $-(CH_2)_3-O-PO_2(OH)-$ $M^+$, and substituted $-(CH_2)_3-O-PO_2(OH)-$, wherein the substituent is

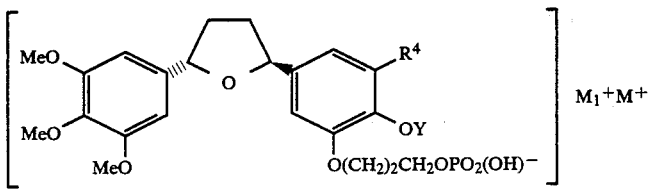

$M_1^+ M^+$ or

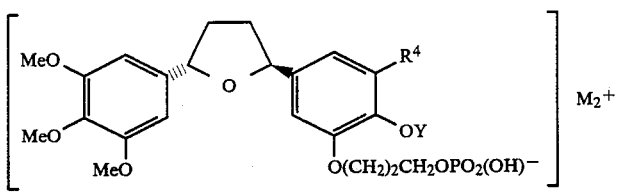

$M_2^+$ wherein M is a pharmaceutically acceptable monovalent cation, $M_1$ is a pharmaceutically acceptable amino acid cation and $M_2$ is a pharmaceutically acceptable di-valent cation.

21. A compound of claim 20 wherein
$R^4$ is $SO_2CH_2COCH_3$,
Y is $-CH_2CH_2CH_3$, and
$R^6$ is (a) $-(CH_2)_3-O-PO_2(OH)- M^+$, wherein M is sodium, potassium, ammonium, lithium, lysine or ornithine, or
(b) substituted $-(CH_2)_3-O-PO_2(OH)-$, wherein the substituent is

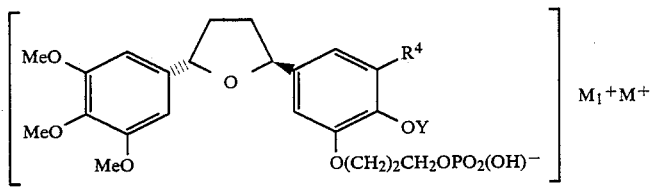

$M_1^+ M^+$ wherein
M is K and $M_1$ is ornithine,
M is Na and $M_1$ is ornithine,
M is Li and $M_1$ is ornithine,
M is K and $M_1$ is lysine,
M is Na and $M_1$ is lysine, or
M is Li and $M_1$ is lysine.

22. A compound according to claim 21 which
(a) (−)-trans-(2S,5S)-[3-(2-Oxopropylsulfonyl)-4-n-propoxy-5-[3-(phosphonooxy)propoxy]phenyl]-5-(3,4,5-trimethoxyphenyl)tetrahydrofuran monopotassium salt,
(b) (−)-trans-(2S,5S)-[3-(2-Oxopropylsulfonyl)-4 -n-propoxy-5-[3-(phosphonooxy)propoxy]phenyl]-5-(3,4,5-trimethoxyphenyl)tetrahydrofuran monolithium salt,
(c) (−)-trans-(2S,5S)-[3-(2-Oxopropylsulfonyl)-4-n-propoxy-5-[3-(phosphonooxy)propoxy]phenyl]-5-(3,4,5-trimethoxyphenyl)tetrahydrofuran monosodium salt, or
(d) (−)-trans-(2S,5S)-[3-(2-Oxopropylsulfonyl)-4-n propoxy-5-[3-(phosphonooxy)propoxy]phenyl]-5-(3,4,5-trimethoxyphenyl)tetrahydrofuran lysine salt.

23. A compound according to claim 22 which is
(−)-trans-(2S,5S)-[3-(2-Oxopropylsulfonyl)-4-n-propoxy-5-[3-(phosphonooxy)propoxy]phenyl]-5-(3,4,5-trimethoxyphenyl)tetrahydrofuran monopotassium salt.

24. A compound according to claim 21 which is
(a) (−)-trans-(2S,5S)-[3-(2-Oxopropylsulfonyl)-4-n-propoxy-5-[3-(phosphonooxy)propoxy]phenyl]-5-(3,4,5-trimethoxyphenyl)tetrahydrofuran potassium ornithine salt, or
(b) (−)-trans-(2S,5S)-[3-(2-Oxopropylsulfonyl)-4-n-propoxy-5-[3-(phosphonooxy)propoxy]phenyl]-5-(3,4,5-trimethoxyphenyl)tetrahydrofuran lysine salt.

25. A pharmaceutical composition for antagonising the effects of PAF which comprises a nontoxic therapeutically effective amount of a compound which is
(a) (2S,5S)-2-[3-((2S)-2-hydroxy-n-propylsulfonyl)-4-n-propoxy-5-(3-hydroxy-n-propoxy)phenyl]-5-(3,4,5-trimethoxyphenyl)tetrahydrofuran, or
(b) (−)(2S,5S)-2-[3-((2S)-2-Hydroxypropyl-sulfonyl)-4-n-propoxy-5-{3-(phosphonooxy)-propoxy}phenyl]-5-(3,4,5-trimethoxyphenyl)tetrahydrofuran.

26. A pharmaceutical composition for antagonising the effects of PAF which comprises a nontoxic therapeutically effective amount of a compound according claim 20.

27. A pharmaceutical composition for according to claim 20 wherein the active agent is
(−)-trans-(2S,5S)-[3-(2-Oxopropylsulfonyl)-4-n-propoxy-5-[3-(phosphonooxy)propoxy]phenyl]-5-(3,4,5-trimethoxyphenyl)tetrahydrofuran monopotassium salt.

28. A method of antagonising the effects of PAF in a subject in need thereof which comprises administering to said subject a nontoxic therapeutically effective amount of a compound which is
(a) (2S,5S)-2-[3-((2S)-2-hydroxy-n-propylsulfonyl)-4-n-propoxy-5-(3-hydroxy-n-propoxy)phenyl]-5-(3,4,5-trimethoxyphenyl)tetrahydrofuran, or (b) (−)(2S,5S)-2-[3-{(2S)-2-Hydroxypropyl-sulfonyl}-4-n-propoxy-5-{3-(phosphonooxy)-propoxy}phenyl]-5-(3,4,5-trimethoxyphenyl)tetrahydrofuran.

29. A method of antagonising the effects of PAF in a subject in need thereof which comprises administering to said subject a nontoxic therapeutically effective amount of a compound according to claim 20.

30. A method of antagonising the effects of PAF in a subject in need thereof which comprises administering to said subject a nontoxic therapeutically effective amount of a compound which is
(−)-trans-(2S,5S)-[3-(2-Oxopropylsulfonyl)-4-n-propoxy-5-[3-(phosphonooxy)propoxy]phenyl]-5-(3,4,5-trimethoxyphenyl)tetrahydrofuran monopotassium salt.

* * * * *